United States Patent [19]

Niewöhner et al.

[11] Patent Number: 5,866,571
[45] Date of Patent: *Feb. 2, 1999

[54] 9-SUBSTITUTED 2-(2-N-ALKOXYPHENYL)-PURIN-6-ONES

[75] Inventors: Ulrich Niewöhner, Wermelskirchen; Erwin Bischoff, Wuppertal; Helmuth Schütz, Wuppertal; Elisabeth Perzborn, Wuppertal; Matthias Schramm, Leverkusen, all of Germany

[73] Assignee: Bayer Aktiengesellschaft, Leverkusen, Germany

[*] Notice: The term of this patent shall not extend beyond the expiration date of Pat. No. 5,861,404.

[21] Appl. No.: 585,996

[22] Filed: Jan. 16, 1996

[30] Foreign Application Priority Data

Apr. 19, 1995 [DE] Germany .................. 195 01 480.4

[51] Int. Cl.$^6$ .................. A61K 31/52; A61K 31/655; C07D 473/30
[52] U.S. Cl. .................. 514/232.5; 514/234.2; 514/262; 544/81; 544/118; 544/265; 544/277
[58] Field of Search .................. 544/265, 277, 544/118, 81; 514/234.2, 262, 232.5

[56] References Cited

U.S. PATENT DOCUMENTS

| 4,451,478 | 5/1984 | Simon et al. ............ 544/277 |
| 5,294,612 | 3/1994 | Bacon et al. ............ 544/262 |
| 5,734,053 | 3/1998 | Terrett ................... 544/265 |

FOREIGN PATENT DOCUMENTS

| 293063 | 1/1988 | European Pat. Off. . |
| 352960 | 7/1989 | European Pat. Off. . |
| 9312095 | 6/1993 | WIPO . |
| 9400453 | 1/1994 | WIPO . |

OTHER PUBLICATIONS

L.R. Krepski, et al., Synthesis, pp. 301–303 (1986).

M. Hoey, et al., Biochemical Pharmacology, vol. 40, pp. 193–202 (1980).

F. Logemann, et al., Chemistry and Industry, (13), pp. 541–542 (1980).

*Primary Examiner*—Mark L. Berch
*Attorney, Agent, or Firm*—Sprung Kramer Schaefer & Briscoe

[57] ABSTRACT

9-Substituted 2-(2-n-alkoxyphenyl)purin-6-ones are prepared by cyclizing correspondingly substituted imidazoles and derivatizing the purines thus obtained. The 9-substituted $^2$-(2-n-alkoxyphenyl)purin-6-ones can be employed as active compounds in medicaments, in particular in medicarnents for treatment of inflammations, thromboembolic diseases and cardiovascular diseases.

16 Claims, No Drawings

9-SUBSTITUTED 2-(2-N-ALKOXYPHENYL)-PURIN-6-ONES

The present invention relates to 9-substituted 2-(2-n-alkoxyphenyl)-purin-6-ones, processes for their preparation and their use in medicaments, in particular for treatment of inflammations, thromboembolic and cardiovascular diseases and diseases of the urogenital system.

Purinones and quinazolinones having a selective cGMP PDE-inhibiting action are known from the publications WO 94/00453 and WO 93/12095.

Phosphodiesterases (PDEs) play an essential role in the regulation of the intracellular cGMP and cAMP level. Of the phosphodiesterase isoenzyme groups PDE I to PDE V described to date [nomenclature according to Beavo and Reifsnyder (cf. Beavo, J. A. and Reifsnyder, D. H., Trends in Pharmacol. Sci. 11, 150–155 (1990))], the Ca-calmodulin-activated PDE I, the cGMP-stimulatable PDE II and the cGMP-specific PDE V are essentially responsible for the metabolism of cgMP. Because of the differing distribution of these cGMP-metabolizing PDEs in tissue, selective inhibitors should raise the cGMP level in the corresponding tissue according to the tissue distribution of the corresponding isoenzyme. This can lead to a specific, antiaggregatory, antispastic, vasodilating, antiarrhythmic and/or antiinflammatory action.

The present invention thus relates to 9-substituted 2-(2-n-alkoxyphenyl)-purin-6-ones of the general formula (I),

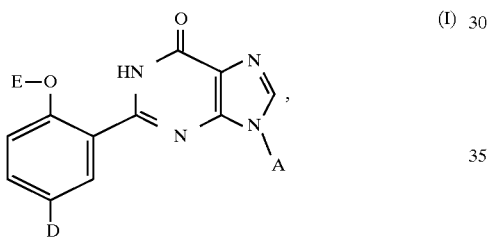

in which
A represents a radical of the formula

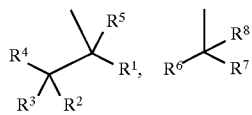

wherein,
a denotes a number 9, 10, 11, 12, 13, 14 or 15,
$R^1$ denotes straight-chain or branched alkyl having 2 to 10 carbon atoms, which is optionally substituted by phenyl, which in turn can be substituted by halogen, nitro, cyano, by straight-chain or branched alkyl having up to 6 carbon atoms or by a group of the formula —$SO_2$—$NR^9R^{10}$,
wherein
$R^9$ and $R^{10}$ are identical or different and denote hydrogen, phenyl or straight-chain or branched alkyl having up to 6 carbon atoms, which is optionally substituted by hydroxyl, or together with the nitrogen atom form a 5- to 6-membered, saturated heterocyclic radical which has up to 2 further heteroatoms from the series consisting of S, N and/or O and is optionally substituted, including via a free N function, by straight-chain or branched alkyl having up to 6 carbon atoms, which in turn can be substituted by hydroxyl, and/or
alkyl is optionally substituted by a group of the formula —$NR^{11}R^{12}$,
wherein
$R^{11}$ and $R^{12}$ have the abovementioned meaning of $R^9$ and $R^{10}$ and are identical to or different from these,
$R^2$ denotes hydrogen, azido, straight-chain or branched alkyl having up to 6 carbon atoms or a group of the formula —$OR^{13}$, O—$SO_2R^{14}$ or —$NR^{15}R^{16}$,
wherein
$R^{13}$ is hydrogen, a hydroxyl-protecting group, straight-chain or branched acyl having up to 6 carbon atoms, benzoyl or straight-chain or branched alkyl having up to 6 carbon atoms, which is optionally substituted by carboxyl or straight-chain or branched alkoxy carbonyl having up to 6 carbon atoms or by a group of the formula —CO—$NR^{17}R^{18}$,
wherein
$R^{17}$ and $R^{18}$ are identical or different and denote hydrogen or straight-chain or branched alkyl having up to 4 carbon atoms,
$R^{14}$ denotes straight-chain or branched having up to 4 carbon atoms or phenyl,
$R^{15}$ and $R^{16}$ are identical or different and denote hydrogen, an arnino-protecting group, straight-chain or branched alkyl or acyl having in each case up to 6 carbon atoms, formyl, benzoyl or a group of the formula —$SO_2R^{19}$,
wherein
$R^{19}$ has the abovementioned meaning of $R^{14}$ and is identical to or different from this,
$R^3$ denotes hydrogen,
or
$R^2$ and $R^3$ together form a radical of the formula =O or =N—$OR^{20}$,
wherein
$R^{20}$ denotes hydrogen or straight-chain or branched alkyl having up to 6 carbon atoms, which is optionally substituted by phenyl or by a group of the formula —$NR^{21}R^{22}$,
wherein
$R^{21}$ and $R^{22}$ are identical or different and denote hydrogen, phenyl or straight-chain or branched alkyl having up to 6 carbon atoms,
$R^4$ denotes hydrogen or straight-chain or branched alkyl having up to 4 carbon atoms,
$R^5$ and $R^8$ are identical or different and denote hydrogen or straight-chain or branched alkyl having up to 3 carbon atoms,
$R^6$ denotes hydrogen or straight-chain or branched alkyl having up to 5 carbon atoms, which is optionally substituted by hydroxyl,
$R^7$ denotes straight-chain or branched alkyl having 2 to 8 carbon atoms, which is substituted by a group of the formula —$NR^{23}R^{24}$,
wherein
$R^{23}$ and $R^{24}$ are identical or different and denote hydrogen or straight-chain or branched alkyl having up to 5 carbon atoms, which is optionally substituted by hydroxyl,
or is substituted by phenyl, which in turn is substituted by the group of the formula —$SO_2$—$NR^{25}R^{26}$,
wherein
$R^{25}$ and $R^{26}$ have the abovementioned meaning of $R^9$ and $R^{10}$, D represents hydrogen or represents a group of the formula —SO$_2$—NR$^{27}$R$^{28}$, wherein R$^{27}$ and R$^{28}$ are identical or different and have the abovementioned meaning of R$^9$ and R$^{10}$ and are identical to or different from these, and E represents straight-chain or branched alkyl having up to 8 carbon atoms, and tautomers and salts thereof.

The substances according to the invention can also be in the form of salts. Physiologically acceptable salts are preferred in the context of the invention.

Physiologically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds of the general formula (I) according to the invention can occur in various stereochemical forms which either behave as mirror images (enantiomers) or do not behave as mirror images (diastereomers). The invention relates both to the antipodes and to the racemic forms as well as the diastereomer mixtures. The racemic forms, like the diastereomers, can be separated into the stereoisomerically uniform constituents in a known manner.

A 5- to 6-membered saturated heterocyclic radical which is bonded via the nitrogen atom and can also contain, as heteroatom, up to 2 oxygen, sulphur and/or nitrogen atoms in general represents piperidyl, morpholinyl, piperazinyl or pyrrolidinyl. Piperidyl and morpholinyl are particularly preferred.

Hydroxyl-protecting group in the context of the abovementioned definition in general represents a protecting group from the series consisting of: trimethylsilyl, triethylsilyl, triisopropylsilyl, tert-butyl-dimethylsilyl, triphenylsilyl or benzyl. Trimethylsilyl, tert-butyl-dimethylsilyl or benzyl are preferred.

Amino-protecting groups in the context of the invention are the customary amino-protecting groups used in peptide chemistry.

These include, preferably: benzyloxycarbonyl, methoxycarbonyl, ethoxycarbonyl, propoxycarbonyl, isopropoxycarbonyl, butoxycarbonyl, isobutoxycarbonyl, tert-butoxycarbonyl, formyl or acetyl.

Preferred compounds are those of the general formula (I), in which

A represents a radical of the formula

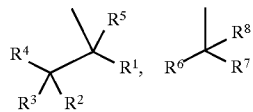

wherein, a denotes a number 9, 10, 11, 12 or 13,

R$^1$ denotes straight-chain or branched alkyl having 2 to 8 carbon atoms, which is optionally substituted by phenyl, which in turn can be substituted by fluorine, chlorine, bromine, nitro, cyano, by straight-chain or branched alkyl having up to 4 carbon atoms or by a group of the formula —SO$_2$—NR$^9$R$^{10}$, wherein R$^9$ and R$^{10}$ are identical or different and denote hydrogen, phenyl or straight-chain or branched alkyl having up to 5 carbon atoms, which is optionally substituted by hydroxyl, or, together with the nitrogen atom, form a morpholinyl, pyrrolidinyl or piperidinyl ring or a piperazinyl ring, which is optionally substituted, including via a free NH function, by straight-chain or branched alkyl having up to 3 carbon atoms, which in turn can be substituted by hydroxyl, and/or alkyl is optionally substituted by a group of the formula —NR$^{11}$R$^{12}$, wherein R$^{11}$ and R$^{12}$ have the abovementioned meaning of R$^9$ and R$^{10}$ and are identical to or different from these, R$^2$ denotes hydrogen, azido, straight-chain or branched alkyl having up to 4 carbon atoms or a group of the formula —OR$^{13}$, —O—SO$_2$-R$^{14}$ or —NR$^{15}$R$^{16}$, wherein R$^{13}$ denotes hydrogen, benzyl, straight-chain or branched acyl having up to 4 carbon atoms, benzoyl or straight-chain or branched alkyl having up to 4 carbon atoms, which is optionally substituted by carboxyl or straight-chain or branched alkoxy carbonyl having up to 4 carbon atoms or by a group of the formula —CO—NR$^{17}$R$^{18}$, wherein R$^{17}$ and R$^{18}$ are identical or different and denote hydrogen or straight-chain or branched alkyl having up to 3 carbon atoms, R$^{14}$ denotes straight-chain or branched alkyl having up to 3 carbon atoms or phenyl, R$^{15}$ and R$^{16}$ are identical or different and denote hydrogen, tert-butoxycarbonyl, benzyloxycarbonyl or straight-chain or branched alkyl or acyl having in each case up to 4 carbon atoms, formyl, benzoyl or a group of the formula —SO$_2$R$^{19}$, wherein R$^{19}$ has the abovementioned meaning of R$^{14}$ and is identical to or different from this, R$^3$ denotes hydrogen, or R$^2$ and R$^3$ together form a radical of the formula =O or =N—OR$^{20}$, wherein R$^{20}$ denotes hydrogen or straight-chain or branched alkyl having up to 4 carbon atoms, which is optionally substituted by phenyl or by a group of the formula —NR$^{21}$R$^{22}$, wherein R$^{21}$ and R$^{22}$ are identical or different and denote hydrogen, phenyl or straight-chain or branched alkyl having up to 4 carbon atoms, R$^4$ denotes hydrogen or straight-chain or branched alkyl having up to 3 carbon atoms, R$^5$ and R$^8$ are identical or different and denote hydrogen or methyl, R$^6$ denotes hydrogen or straight-chain or branched alkyl having up to 3 carbon atoms, which is optionally substituted by hydroxyl, R$^7$ denotes straight-chain or branched alkyl having 2 to 6 carbon atoms, which is substituted by a group of the formula —NR$^{23}$R$^{24}$, wherein R$^{23}$ and R$^{24}$ are identical or different and denote hydrogen or straight-chain or branched alkyl having up to 4 carbon atoms, which is optionally substituted by hydroxyl,
or is substituted by phenyl, which in turn is substituted by a group of the formula $-SO_2-NR^{25}R^{26}$,
wherein
$R^{25}$ and $R^{26}$ are identical or different and have the abovementioned meaning of $R^9$ and $R^{10}$,
D represents hydrogen, or represents a group of the formula $-SO_2-NR^{27}R^{28}$,
wherein
$R^{27}$ and $R^{28}$ are identical or different and have the abovementioned meaning of $R^9$ and $R^{10}$ and are identical to or different from these, and
E represents straight-chain or branched alkyl having up to 6 carbon atoms,
and tautomers and salts thereof.

Particularly preferred compounds are those of the general formula (I), in which
A represents a radical of the formula

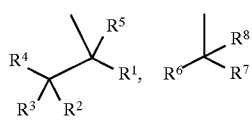

wherein,
a denotes a number 9, 10, 11 or 12,
$R^1$ denotes straight-chain or branched alkyl having 2 to 7 carbon atoms, which is optionally substituted by phenyl, which in turn can be substituted by fluorine, chlorine, bromine, nitro, cyano, by straight-chain or branched alkyl having up to 3 carbon atoms or by a group of the formula $-SO_2-NR^9R^{10}$,
wherein
$R^9$ and $R^{10}$ are identical or different and denote hydrogen, phenyl or straight-chain or branched alkyl having up to 4 carbon atoms, which is optionally substituted by hydroxyl, or, together with the nitrogen atom, form a morpholinyl, pyrrolidinyl or piperidinyl ring or a piperazinyl ring, which is optionally substituted, including via free NH function, by straight-chain or branched alkyl having up to 3 carbon atoms, which in turn can be substituted by hydroxyl,
and/or
alkyl is optionally substituted by a group of the formula $-NR^{11}R^{12}$,
wherein
$R^{11}$ and $R^{12}$ have the abovementioned meaning of $R^9$ and $R^{10}$ and are identical to or different from these,
$R^2$ denotes hydrogen, azido, straight-chain or branched alkyl having up to 3 carbon atoms or a group of the formula $-OR^{13}$, $-OSO_2R^{14}$ or $-NR^{15}R^{16}$,
wherein
$R^{13}$ denotes hydrogen, straight-chain or branched acyl having up to 3 carbon atoms, benzoyl or straight-chain or branched alkyl having up to 3 carbon atoms, which is optionally substituted by carboxyl or straight-chain or branched alkoxycarbonyl having up to 3 carbon atoms or by a group of the formula $-CO-NR^{17}R^{18}$,
wherein
$R^{17}$ and $R^{18}$ are identical or different and denote hydrogen, methyl or ethyl,
$R^{14}$ denotes straight-chain or branched alkyl having up to 3 carbon atoms or phenyl, $R^{15}$ and $R^{16}$ are identical or different and denote hydrogen, tert-butoxycarbonyl, straight-chain or branched alkyl or acyl having in each case up to 3 carbon atoms, formyl, benzoyl or a group of the formula $-SO_2R^{19}$,
wherein
$R^{19}$ has the abovementioned meaning of $R^{14}$ and is identical to or different from this,
$R^3$ denotes hydrogen,
or
$R^2$ and $R^3$ together form a radical of the formula $=O$ or $=N-OR^{20}$,
wherein
$R^{20}$ denotes hydrogen or straight-chain or branched alkyl having up to 4 carbon atoms, which is optionally substituted by phenyl or by a group of the formula $-NR^{21}R^{22}$,
wherein
$R^{21}$ and $R^{22}$ are identical or different and denote hydrogen, phenyl or straight-chain or branched alkyl having up to 3 carbon atoms,
$R^4$ denotes hydrogen or straight-chain or branched alkyl having up to 3 carbon atoms,
$R^5$ and $R^8$ are identical or different and denote hydrogen or methyl,
$R^6$ denotes hydrogen or straight-chain or branched alkyl having up to 3 carbon atoms, which is optionally substituted by hydroxyl,
$R^7$ denotes straight-chain or branched alkyl having 2 to 6 carbon atoms, which is substituted by a group of the formula $-NR^{23}R^{24}$,
wherein
$R^{23}$ and $R^{24}$ are identical or different and denote hydrogen or straight-chain or branched alkyl having up to 3 carbon atoms, which is optionally substituted by hydroxyl, or is substituted by phenyl, which in turn is substituted by the group of the formula $-SO_2-R^{25}R^{26}$,
wherein
$R^{25}$ and $R^{26}$ have the abovementioned meaning of $R^9$ and $R^{10}$,
D represents hydrogen, or represents a group of the formula $-SO_2-NR^{27}R^{28}$,
wherein
$R^{27}$ and $R^{28}$ are identical or different and have the abovementioned meaning of $R^9$ and $R^{10}$ and are identical to or different from these, and
E represents straight-chain or branched alkyl having up to 5 carbon atoms,
and tautomers and salts thereof.

A process has furthermore been found for the preparation of the compounds of the general formula (I) according to the invention, characterized in that compounds of the general formula (II)

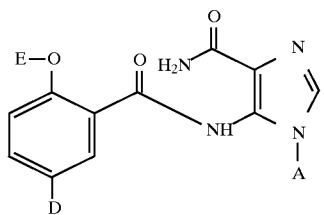

in which
D, E and A have the abovementioned meaning,
are first cyclized in inert solvents and in the presence of a base, and in the case where D=H, the corresponding sulphonic acid chlorides are first prepared by reaction with chlorosulphonic acid and the corresponding sulphonamides are then prepared with amines ($NR^{25}R^{26}$), and the substituents $R^1$–$R^8$ are introduced or derivatized by customary methods, such as, for example alkylation, acylation, amination, oxidation or azide exchange.

The process according to the invention can be illustrated by way of example by the following equations:

ether, dioxane, tetrahydrofuran or glycol mono- or dimethyl ether, ethyl acetate, toluene, acetonitrile, hexamethylphosphoric acid triamide, pyridine and acetone. It is of course possible to employ mixtures of the solvents. Tetrahydrofuran, toluene or pyridine are particularly preferred.

Suitable solvents for the cyclization are the customary organic solvents. These include, preferably, alcohols, such as methanol, ethanol, propanol, isopropanol or butanol, or Equation A:

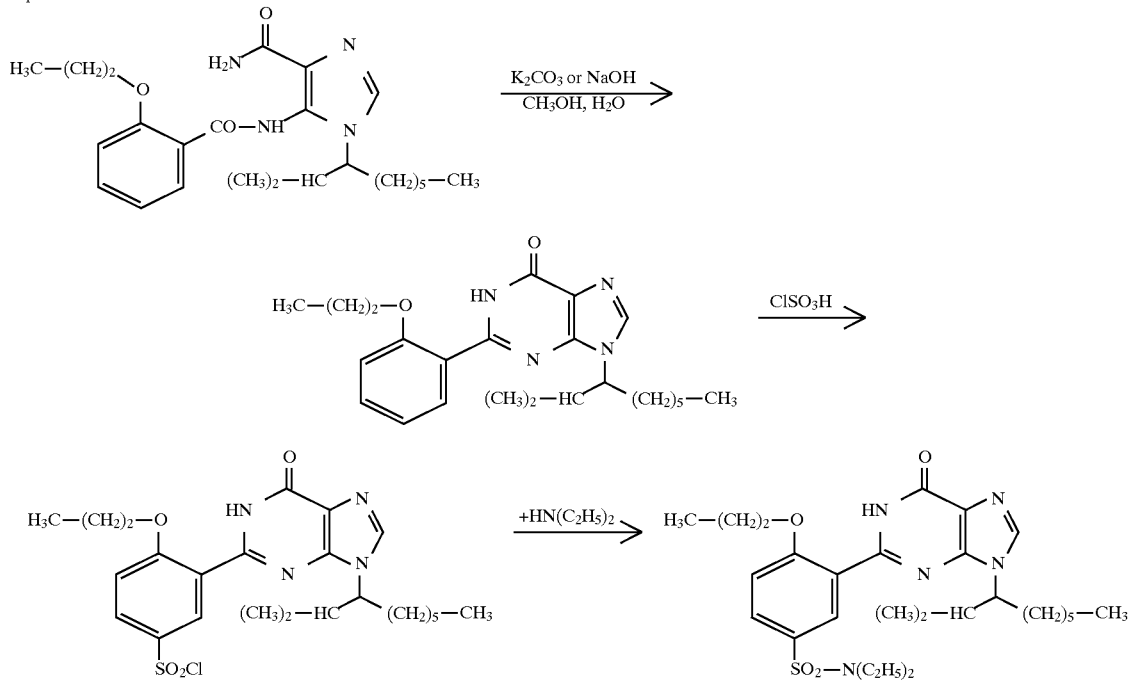

Equation B:

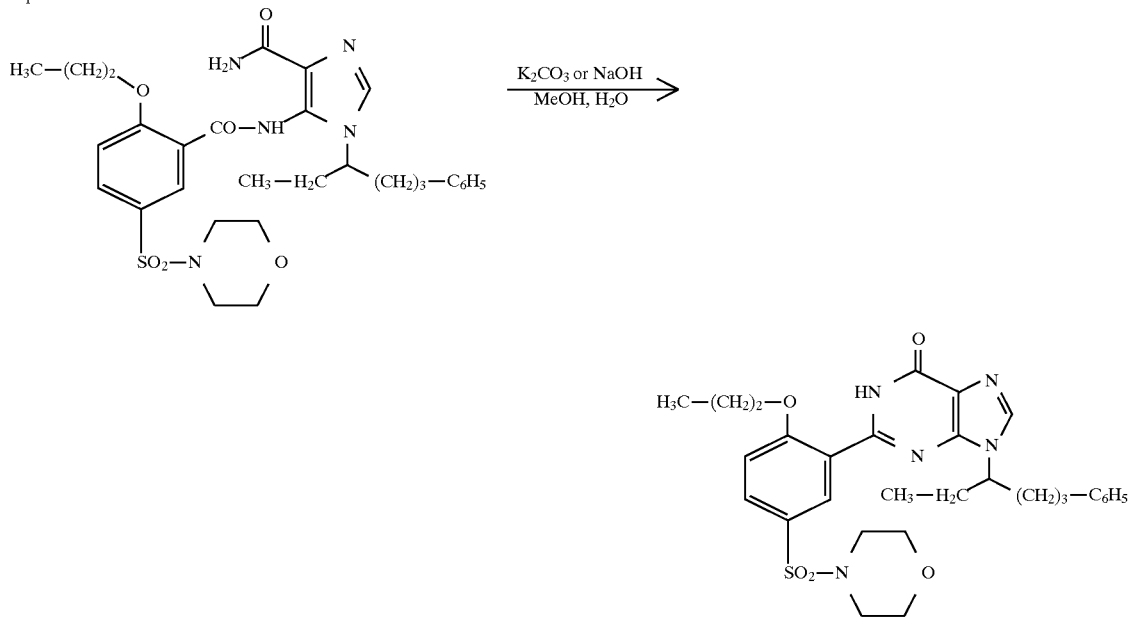

Inert organic solvents which do not change under the reaction conditions are suitable for the process. These include, preferably, ethers, such as, for example, diethyl ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

Suitable bases for the cyclization are the customary inorganic bases. These include, preferably, alkali metal hydroxides or alkaline earth me droxides, such as, for example, sodium hydroxide, potassium hydroxide or barium hydroxide, or alkali metal carbonates, such as sodium carbonate or potassium carbonate or sodium bicarbonate, or alkali metal alcoholates, such as sodium methanolate, sodium ethanolate, potassium methanolate, potassium ethanolate or potassium tert-butanolate. Potassium carbonate and sodium hydroxide are particularly preferred.

In carrying out the cyclization, the base is in general employed in an amount of 2 to 6 mol, preferably 3 to 5 mol, per mole of the compounds of the formula (II).

The cyclization is in general carried out in a temperature range from 0° C. to 160° C., preferably at the boiling point of the particular solvent.

The cyclization is in general carried out under normal pressure. However, it is also possible to carry out the process under increased pressure or under reduced pressure (for example in a range from 0.5 to 5 bar).

The chlorosulphonation is carried out either without a solvent or in the presence of one of the abovementioned inert solvents.

The preparation of the sulphonamides is in general carried out in one of the abovementioned solvents, preferably in tetrahydrofuran or methylene chloride.

The chlorosulphonation and the amidation are in general carried out in a temperature range from −20° C. to +80° C., preferably −10° C. to +30° C., under normal pressure.

Suitable bases for this are, in addition to the abovementioned bases, preferably in some cases triethylamine and/or dimethylaminopyridine, DBU or DABCO. It is also possible for the amine employed to be used in excess.

The base is employed in an amount of 0.5 mol to 10 mol, preferably 1 mol to 3 mol per mole of the corresponding chlorosulphonic acid.

The alkylation is in general carried out with alkylating agents, such as, for example, ($C_1$–$C_{10}$)-alkyl halides, sulphonic acid esters or substituted or unsubstituted ($C_1$–$C_{10}$) -dialkyl- or ($C_1$–$C_{10}$)-diarylsulphonates, preferably methyl iodide or dimethyl sulphate.

Suitable solvents for the alkylation are likewise the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, dimethylformamide, hexamethylphosphoric acid triamide, acetonitrile or acetone. It is also possible to use mixtures of the solvents mentioned. Methylene chloride is preferred.

The alkylation is carried out in the abovementioned solvents at temperatures from 0° C. to +150° C., preferably at room temperature to +100° C., under normal pressure.

The amino-protecting groups are split off in a manner known per se under acid or basic conditions, or reductively by catalytic hydrogenation, for example with Pd/C in organic solvents, such as ethers, for example tetrahydrofuran or dioxane, or alcohols, for example methanol, ethanol or isopropanol.

The hydroxyl-protecting group is split off from the corresponding esters by customary hydrolytic methods.

The reaction with alkyl sulphonic acid chlorides is carried out, starting from the corresponding free hydroxy compounds, in one of the abovementioned solvents and one of the bases, preferably with methylene chloride and triethylamine in a temperature range from −20° C. to +20° C., preferably 0° C., under normal pressure.

The introduction of the azide radical is in general carried out by reaction of the corresponding alkylsulphonyloxy-substituted compounds with sodium azide in one of the abovementioned solvents, preferably dimethylformamide, in a temperature range from 50° C. to +120° C., preferably 100° C., under normal pressure.

The reduction of azido-substituted compounds to give the corresponding free amines is in general carried out by hydrogenation in one of the abovementioned alcohols, preferably methanol, with hydrogen in the presence of a palladium catalyst, preferably Pd/C, in a temperature range from 0° C. to +50° C., preferably 25° C.

The hydrogenation is in general carried out under normal pressure.

The acylations are carried out, starting from the corresponding free amino or hydroxy compounds, in one of the abovementioned solvents, preferably methylene chloride, and in the presence of one of the abovementioned bases, preferably triethylamine, with addition of dimethylaminopyridine (DMAP), in a temperature range from 0° C. to +80° C., preferably at +20° C. to +40° C., under normal pressure.

The ketones are prepared by known methods (Swern oxidation) starting from the corresponding hydroxy compounds.

The oxime formation is in general carried out by reaction of the corresponding ketone with hydroxylamines in one of the abovementioned alcohols, preferably methanol, at the reflux temperature under normal pressure.

The enantiomerically pure compounds are accessible by customary methods, for example by chromatography or the racemic compounds of the general formula (I) on chiral phases.

The compounds of the general formula (II) are known in some cases or are new and can be prepared by a procedure in which compounds of the general formula (III)

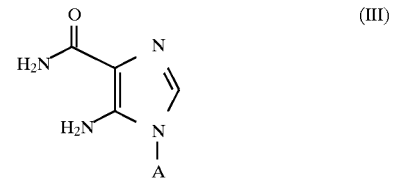

in which

A has the abovementioned meaning, are reacted with 2-n-alkoxybenzoic acid chlorides of the general formula (IV)

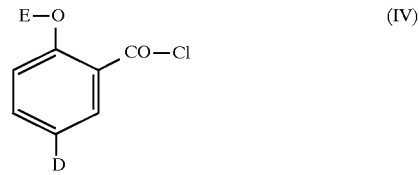

in which

D and E have the abovementioned meaning, in inert solvents and in the presence of a base.

Suitable solvents are the abovementioned solvents, toluene and tetrahydrofuran being preferred.

Suitable bases are in general alkali metal hydrides or alcoholates, such as, for example, sodium hydride or potassium tert-butylate, or cyclic amines, such as, for example, piperidine, pyridine, dimethylaminopyridine or $C_1$–$C_4$-alkylamine, such as, for example, triethylamine. Sodium hydride, pyridine and dimethylaminopyridine are preferred.

The base is in general employed in an amount of 1 mol 4 mol, preferably 1.2 mol to 3 mol, in each case per mole of the compounds of the general formula (III).

The reaction temperature can in general be varied within a relatively wide range. The reaction is in general carried out in a range from –20° C. to 200° C., preferably 0° C. to 25° C.

In one variant, the reaction is carried out in pyridine, to which a catalytic amount of DMAP is added. If appropriate, toluene can also be added.

The compounds of the general formula (IV) are known per se.

The compounds of the general formula (III) are new in most cases and can be prepared, for example, by a procedure in which
2-amino-2-cyanoacetamide of the formula (V)

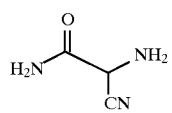

is reacted with compounds of the general formula (VI)

in which
A has the abovementioned meaning,
in inert solvents in the presence of triethyl orthoformate.

Suitable solvents for the individual steps of the processes are the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, dimethylformamide, hexamethylphosphoric acid triamide, acetonitrile, acetone or dimethoxyethane. It is also possible to use mixtures of the solvents mentioned. Acetonitrile is particularly preferred.

The process according to the invention is in general carried out in a temperature range from 0° C. to +180° C., preferably +30° C. to +150° C.

The process steps according to the invention are in general carried out under normal pressure. However, it is also possible to carry out the process steps under increased pressure or under reduced pressure (for example in a range from 0.5 to 5 bar).

The compound of the formula (V) is known [cf. Logemann, G. Shaw, Chemistry and Industry, 1980 (13), 541–542].

The amines of the general formula (VI) are known in some cases or are new and they can then be prepared by known methods [cf. L. R. Krepski et al., Synthesis, 1986, 301–303].

The compounds of the general formula (I) according to the invention display an unforeseeable, valuable pharmacological action spectrum.

They inhibit either one or more of the cGMP-metabolizing phosphodiesterases (PDE I, PDE II and PDE V). This leads to a different increase in cGMP. An increase in the cGMP level can lead to an antithrombotic, vasodilatory, antiarryhthmic and/or antiinflammatory action. The selectivity is also determined by the distribution of the isoenzymes in the tissue.

The compounds according to the invention furthermore intensify the action of substances, such as, for example, EDRF (endothelium-derived relaxing factor) and ANP (atrial natriuretic peptide), which increase the cGMP level.

They can therefore be employed in medicaments for treatment of inflammatory diseases, such as, for example, asthma, inflammatory dermatoses, for treatment of high blood pressure, stable and unstable angina, peripheral and cardiac vascular diseases and of arrhythmias, for treatment of thromboembolic diseases and ischaemias, such as myocardial infarction, cerebral stroke, transitory and ischaemic attacks, angina pectoris, peripheral circulatory disturbances, prevention of restenoses, such as after thrombolysis treatment, percutaneous transluminal angioplasties (PTA) and bypass, percutaneous transluminal coronary angioplasties (PTCA), bypass, septic shock and diseases of the urogenital system, such as, for example prostate hypertrophy, impotence and incontinence.

Activity of the phosphodiesterases (PDE's)

The cGMP-stimulatable PDE II, the cGMP-inhibitable PDE III and the cAMP-specific PDE IV were isolated from either the porcine or the bovine myocardium. The Ca-calmodulin-stimulatable PDE I was isolated from porcine aorta or porcine brain. The cGMP-specific PDE V was obtained from porcine small intestine, porcine aorta and/or human blood platelets. Purification was carried out by anion exchange chromatography on MonoQ$^R$ Pharmacia essentially by the method of M. Hoey and Miles D. Houslay, Biochemical Pharmacology, Volume 40, 193–202 (1990).

The enzyme activity is determined in a test batch of 100 µl in 20 mM Tris/HCl buffer of pH 7.5 which contains 5 mM $MgCl_2$, 0.1 mg/ml of bovine serum albumin and either 800 Bq of $^3$HcAMP or $^3$HcGMP. The final concentration of the corresponding nucleotides is $10^{-6}$ mol/l. The reaction is started by addition of the enzyme and the amount of enzyme is chosen such that about 50% of the substrate is reacted during the incubation time of 30 minutes. In order to test the cGMP-stimulatable PDE II, $^3$HcAMP is used as the substrate and $10^{-6}$ mol/l of non-labelled cGMP is added to the batch. In order to test the Ca-calmodulin-dependent PDE I, 1 µM $CaCl_2$ and 0.1 µM calmodulin are also added to the reaction batch. The reaction is stopped by addition of 100 µl of acetonitrile which contains 1 mM cAMP and 1 mM AMP. 100 µl of the reaction batch are separated on the PLC and the cleavage products are determined quantitatively "on line" with a flow-through scintillation counter. The substance concentration at which the rate of reaction is reduced by 50% is measured.

| Inhibition of the phosphodiesterases in vitro | | | |
|---|---|---|---|
| Example No. | PDE I IC$_{50}$ [µM] | PDE II IC$_{50}$ [µM] | PDE V IC$_{50}$ [µM] |
| 3 | 50 | 6 | 0.1 |
| 4 | 2 | 1 | 5 |
| 5 | 1 | 0.5 | 2 |
| 11 | 0.5 | 0.3 | 0.5 |
| 37 | 2 | 2 | 1 |
| 57 | 0.3 | 0.3 | 0.1 |

The antihypertensive activity was measured after intravenous administration to SHR rats.

To determine the cyclic nucleotides, heart and aorta tissue was removed and deep-frozen immediately. The samples were powdered under liquid $N_2$ and extracted with 70% ethanol and the content of cGMP and cAMP was determined using commercial radioimmunoassays (Amersham).

The erection-inducing action was measured on anaesthetized rabbits (C. G. Stief et al., World Journal Urology 1990, pages 233–236).

The substances were administered in dosages of 0.1 to 10 mg/kg either directly into the corpus cavernosum or intraduodenally, rectally, orally, transdermally or intravenously.

The new active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. The therapeutically active compound should in each case be present here in a concentration of about 0.5 to 90% by weight of the total mixture, i.e. in amounts which are sufficient to achieve the stated dosage range.

The formulations are prepared, for example, by extending the active compounds with solvents and/or carriers, if appropriate using emulsifying agents and/or dispersing agents, and in the case where water is used as the diluent, for example, organic solvents can be used as auxiliary solvents if appropriate.

The formulations are administered in the customary manner, preferably orally, parenterally, transdermally, perlingually or intravenously.

In general, it has proved advantageous in the case of intravenous administration to administer amounts of about 0.01 to 10 mg/kg, preferably about 0.1 to 10 mg/kg of body weight to achieve effective results.

Nevertheless, it may be necessary, if appropriate, to deviate from the amounts mentioned, and in particular as a function of the body weight or the nature of the administration route, of the behaviour of the individual towards the medicament, of the nature of the formulation thereof and of the time or interval at which administration takes place. Thus, in some cases it may be sufficient to manage with less than the abovementioned minimum amount, while in other cases the upper limit mentioned must be exceeded. In the case of administration of relatively large amounts, it may be advisable to divide these into several individual doses over the course of the day.

Starting compounds

General working instructions for the preparation of 1-substituted 5-(2-n-alkoxybenzoylamino)-imidazole-4-carboxamides of the formula (IV)

Method A:

10 mmol of 1-substituted 5-amino-imidazole-4-carboxamide and 15 mmol of NaH (if one of the abovementioned radicals $R^1$, $R^2$, $R^3$, $R^4$, $R^5$, $R^6$, $R^7$ or $R^8$ contains a hydroxyl group, 30 mmol of NaH are employed) are stirred in 50 ml of absolute tetrahydrofuran at 20° C. for 3 hours (in the case of sparingly soluble imidazoles, the mixture is refluxed for up to 12 hours). 10 mmol of 2-n-alkoxybenzoic acid chloride (or 20 mmol if a hydroxyl group is present) in 25 ml of absolute tetrahydrofuran are added dropwise at 20° C. and the mixture is stirred at room temperature overnight. It is evaporated, the residue is taken up in ethyl acetate and the mixture is extracted by shaking with water. The organic phase is dried over $Na_2SO_4$ and evaporated and the residue is purified by recrystallization or flash chromatography.

If the 5-amino-imidazole-4-carboxamide contains a free hydroxyl group in the radicals $R^1$, $R^2$, $R^3$, $R^4$, $R^5$, $R^6$, $R^7$ or $R^8$, this is in the form of the 2-n-alkoxybenzoic acid ester, which can be hydrolysed by the known method (1N NaOH, $CH_3OH$). However, it is also possible for the ester to be cyclized directly with NaOH as the base to give the purinones, the ester likewise being hydrolysed.

Method B:

10 mmol of 1-substituted 5-amino-imidazole-4-carboxamide and 50 mg of DMAP are initially introduced into 20 ml of dry pyridine at room temperature. A solution of 10 mmol of n-alkoxybenzoic acid chloride in 10 ml of absolute toluene is added dropwise and the mixture is stirred at room temperature until, in the thin-layer chromatogram, the reaction has ended (30 minutes to 16 hours). The precipitate is filtered off and the solvent is removed in a rotary evaporator in vacuo. The residue is taken up in 30 ml of methylene chloride and the mixture is washed with 30 ml of 1N HCl and 30 ml of $H_2O$. After drying over $Na_2SO_4$, the mixture is evaporated in vacuo and the residue is purified by flash chromatography or recrystallization.

The 1-substituted 5-(2-n-alkoxybenzoylamino)-imidazole-5-carboxamides listed in Table 1 are prepared in accordance with these instructions:

TABLE 1

| Example No. | A | D | Yield (% of theory) | Melting point (°C.)/$R_f$ |
|---|---|---|---|---|
| I | 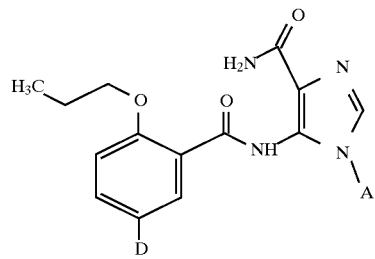 | H | 41 | |

TABLE 1-continued

[Structure: 2-propoxy-benzamide substituted at 5-position by D, N-linked to a pyrazole-carboxamide bearing substituent A on the ring nitrogen]

| Example No. | A | D | Yield (% of theory) | Melting point (°C.)/R$_f$ |
|---|---|---|---|---|
| II | HOCH$_2$-CH(CH$_3$)-(CH$_2$)$_5$-CH$_3$ | H | 38 | |
| III | CH$_3$-CH(OH)-CH(CH$_3$)-(CH$_2$)$_5$-CH$_3$ | H | 52 | |
| IV | CH$_3$-CH(OH)-CH(CH$_3$)-CH$_2$-CH$_2$-C$_6$H$_5$ | H | 57 | |
| V | CH$_3$-CH(OH)-CH(CH$_3$)-(CH$_2$)$_3$-C$_6$H$_5$ | H | 11 | 104 (ether) |
| VI | CH$_3$-CH(OH)-CH(CH$_3$)-(CH$_2$)$_4$-C$_6$H$_5$ | H | 12 | |
| VII | CH$_3$-CH(OH)-CH(CH$_3$)-(CH$_2$)$_5$-C$_6$H$_5$ | H | 41 | |
| VIII | CH$_3$-CH(CH$_3$)-(CH$_2$)$_5$-CH$_3$ | H | 30 | |
| IX | CH$_3$-CH$_2$-CH(CH$_3$)-(CH$_2$)$_5$-CH$_3$ | H | 26.6 | |
| X | CH$_3$-CH(CH$_3$)-C(CH$_3$)H-(CH$_2$)$_5$-CH$_3$ | H | 46 | |
| XI | CH$_3$-CH(CH$_3$)-(CH$_2$)$_3$-C$_6$H$_5$ | H | 30 | |

TABLE 1-continued

| Example No. | A | D | Yield (% of theory) | Melting point (°C.)/$R_f$ |
|---|---|---|---|---|
| XII | H₃C-CH(CH₃)-CH₂-CH₂-CH₂-C₆H₅ | H | 50 | |
| XIII | H₃C-CH(CH₃)-CH(CH₃)-CH₂-CH₂-C₆H₅ | H | 26 | |
| XIV | -N(C₂H₅)₂ propyl | H | 27 | |
| XV | -(CH₂)₁₁-CH₃ | H | 41 | |
| XVI | -CH₂CH₂CH₂CH₂-N(CH₃)-CH₂CH₂OH | H | 8 | |
| XVI | -CH₂CH₂CH₂CH₂-N(CH₃)-CH₂CH₂OH | H | 8 | |
| XVII | H₃C-CH(CH₃)-CH₂-CH₂-CH₂-C₆H₅ | -O₂S-N(morpholine) | 27 | |
| XVIII | H₃C-CH(CH₃)-CH(CH₃)-CH₂-CH₂-C₆H₅ | -O₂S-N(morpholine) | 33 | |
| XIX | H₃C-CH(OH)-CH(CH₃)-CH₂-CH₂-C₆H₅ | -O₂S-N(morpholine) | 53 | |
| XX | H₃C-CH(CH₃)-CH₂-CH₂-C₆H₅ | -O₂S-N(morpholine) | 38 | |

PREPARATION EXAMPLES

General working instructions for 9-substituted 2-(2-n-alkoxyphenyl)purin-6-ones of the general formula (I)

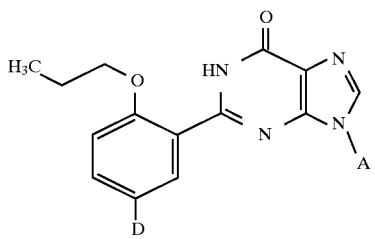

10 mmol of the 1-substituted 5-(2-n-alkoxybenzoylamino)-imidazole-4-carboxamide (IV) and 40 mmol of $K_2CO_3$ are refluxed overnight in a mixture of 100 ml of ethanol and 50 ml of water. The solvent is distilled off in vacuo, the residue is taken up in ethyl acetate and the mixture is extracted twice by shaking with water. After the organic phase has been dried with sodium sulphate, it is evaporated and the residue is purified by recrystallization or flash chromatography.

The compounds listed in Table II are prepared in accordance with these instructions:

TABLE II

| Example No. | A | D | Yield (% of theory) | Melting point (°C.)/$R_F$ |
|---|---|---|---|---|
| 1 | (2-methylpentyl with OH) | H | 63 | 186 |
| 2 | (2-methylheptyl with OH) | H | 87 | 0.33[a] |
| 3 | (3-methyl alcohol chain) | H | 67 | 113 |
| 4 | (methyl-phenethyl alcohol) | H | 39 | 82 |
| 5 | (methyl-phenylpropyl alcohol) | H | 51 | 104 |
| 6 | (methyl-phenylbutyl alcohol) | H | 27 | 68 |

TABLE II-continued

| Example No. | A | D | Yield (% of theory) | Melting point (°C.)/R_f |
|---|---|---|---|---|
| 7 | H₃C-CH(OH)-CH(CH₃)-(CH₂)₄-C₆H₅ | H | 31 | 91 |
| 8 | H₃C-CH(CH₃)-(CH₂)₄-CH₃ | H | 75 | 0.58[a] |
| 9 | H₃C-CH₂-CH(CH₃)-(CH₂)₄-CH₃ | H | 54 | 0.6[a] |
| 10 | H₃C-C(CH₃)(CH₃)-(CH₂)₄-CH₃ | H | 58 | 0.44[a] |
| 11 | H₃C-CH(CH₃)-(CH₂)₃-C₆H₅ | H | 95 | 0.54[a] |
| 12 | H₃C-CH₂-CH(CH₃)-(CH₂)₃-C₆H₅ | H | 71 | 0.58[a] |
| 13 | H₃C-CH(CH₃)-CH(CH₃)-(CH₂)₃-C₆H₅ | H | 63 | 0.59[a] |
| 14 | -(CH₂)₃-N(C₂H₅)₂ | H | 50 | 143 |
| 15 | -(CH₂)₁₁-CH₃ | H | 42 | 80 |
| 16 | -(CH₂)₃-N(CH₃)-CH₂CH₂OH | H | 56 | 188 |
| 17 | -(CH₂)₃-N(CH₃)-CH₂CH₂OH | H | 23 | 0.33[a] |
| 18 | H₃C-CH₂-CH(CH₃)-(CH₂)₃-C₆H₅ | —O₂S—N(morpholine) | 80 | 165 |

TABLE II-continued

| Example No. | A | D | Yield (% of theory) | Melting point (°C.)/$R_f$ |
|---|---|---|---|---|
| 19 | H₃C-CH(CH₃)-CH₂-CH₂-CH₂-C₆H₅ | —O₂S—N(morpholine) | 33 | 0.44[b] |
| 20 | H₃C-CH(OH)-CH(CH₃)-CH₂-CH₂-C₆H₅ | —O₂S—N(morpholine) | 25 | 172 |
| 21 | H₃C-CH(CH₃)-CH₂-CH₂-CH₂-C₆H₅ | —O₂S—N(morpholine) | 57 | 170 |

[a] Mobile phase: $CH_2Cl_2$/MeOH 10:1
[b] Mobile phase: toluene/acetone 1:1

Example 22

9-(2-Methanesulphonyloxy-3-nonyl)-2-(2-n-propoxy-phenyl)-purin-6-one

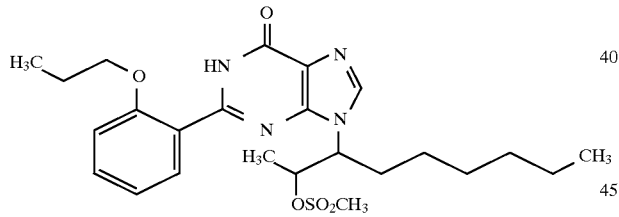

412 mg (1 mmol) of 9-(2-hydroxy-3-nonyl)-2-(2-n-propoxyphenyl)-purin-6-one (Example 3) are cooled to 0° C. in 10 ml of $CH_2Cl_2$. After addition of 0.5 ml of triethylamine, 138 mg (1.2 mmol) of methanesulphonyl chloride in 2 ml of $CH_2Cl_2$ are added dropwise and the mixture is subsequently stirred for 30 minutes. It is poured onto 20 ml of ice-water, the organic phase is separated off and the aqueous phase is extracted once more with 20 ml of $CH_2Cl_2$. The combined $CH_2Cl_2$ phases are dried over $Na_2SO_4$ and evaporated in vacuo and the oily residue is crystallized by trituration with ether.

Melting point: 158° C.
Yield: 380 mg (81%)

Example 23

9-(2-Methanesulphonyloxy-5-phenyl-3-pentyl)-2-(2-n-propoxyphenyl)-purin-6-one

The title compound is prepared analogously to the instructions of Example 22, starting from 9-(2-hydroxy-5-phenyl-3-methyl)-2-(2-n-propoxyphenyl)-purin-6-one (Example 4).
$R_f$=0.52 ($CH_2Cl_2$/$CH_3OH$ 10:1)
Yield: 95.3%

Example 24

9-(2-Methanesulphonyloxy-6-phenyl-3-hexyl)-2-(2-n-propoxyphenyl)-purin-6-one

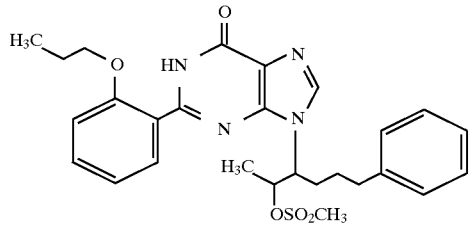

The title compound is prepared analogously to the instructions of Example 22, starting from 9-(2-hydroxy-6-phenyl-3-hexyl)-2-(2-n-propoxyphenyl)-purin-6-one (Example 5).
$R_f$=0.52 (CH$_2$Cl$_2$/CH$_3$OH 10:1)
Yield: 82.7%

Example 25

9-(2-Methanesulphonyloxy-7-phenyl-3-heptyl)-2-(2-n-propoxyphenyl)-purin-6-one

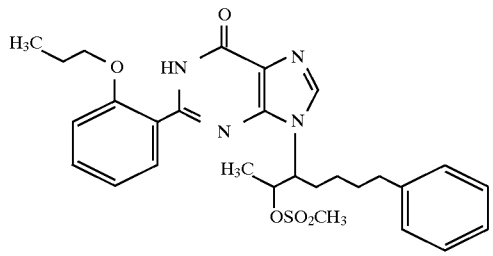

The title compound is prepared analogously to the instructions of Example 22, starting from 9-(2-hydroxy-7-phenyl-3-heptyl)-2-(2-n-propoxyphenyl)-purin-6-one (Example 6).
$R_f$=0.55 (CH$_2$Cl$_2$/CH$_3$OH 10:1)
Yield: 90.3%

Example 26

9-(2-Methanesulphonyloxy-8-phenyl-3-octyl)-2-(2-n-propoxyphenyl)-purin-6-one

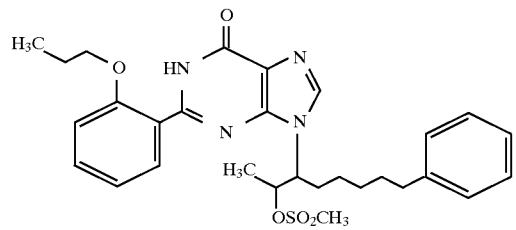

The title compound is prepared analogously to the instructions of Example 22, starting from 9-(2-hydroxy-8-phenyl-3-octyl)-2-(2-n-propoxyphenyl)-purin-7-one (Example 7).
$R_f$=0.58 (CH$_2$Cl$_2$/CH$_3$OH 10:1)
Yield: 89%

Example 27

9-(1-Methanesulphonyloxy-5-phenyl-2-pentyl)-2-(2-n-propoxyphenyl)-purin-6-one

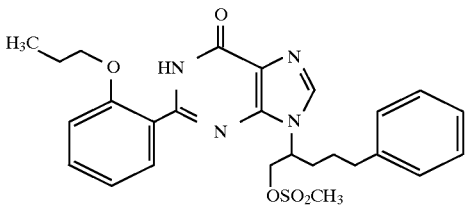

The title compound is prepared analogously to the instructions of Example 22, starting from 9-(1-hydroxy-5-phenyl-3-pentyl)-2-(2-n-propoxyphenyl)-purin-6-one (Example 17).
$R_f$=0.49 (CH$_2$Cl$_2$/CH$_3$OH 10:1)
Yield: 28.5

Example 28

9-(2-Methanesulphonyloxy-3-nonyl)-2-(2-n-propoxy-5-morpholinosulphonyl-phenyl)-purin-6-one

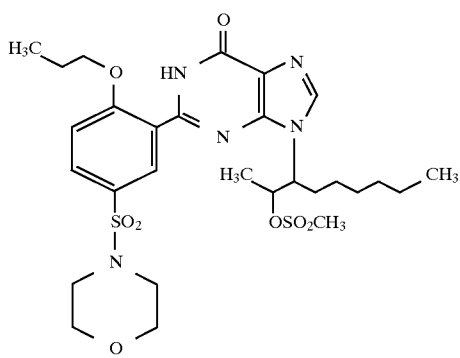

The title compound is prepared analogously to the instructions of Example 22, starting from 9-(2-hydroxy-3-nonyl)-2-(2-n-propoxy-5-morpholinosulphonyl-phenyl)-purin-6-one (Example 20).
$R_f$=0.48 (CH$_2$Cl$_2$/CH$_3$OH 10:1)
Yield: 51.4%

Example 29

9-(2-Azido-3-nonyl)-2-(2-n-propoxyphenyl)-purin-6-one

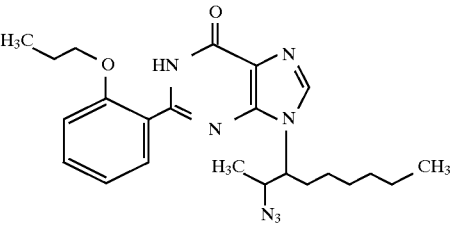

474 mg (1 mmol) of 9-(2-methanesulphonyloxy-3-nonyl)-2-(2-n-propoxyphenyl)-purin-6-one (Example 22) and 78 mg (1.2 mmol) of sodium azide are stirred in 5 ml of dimethylformamide at 100° C. for 6 hours (monitoring by thin-layer chromatography).

After cooling, 20 ml of ethyl acetate are added and the mixture is extracted by shaking 3 times with 50 ml of water each time and once with 50 ml of saturated NaCl solution. After drying over Na$_2$SO$_4$, the organic phase is evaporated in vacuo and the residue is purified by flash chromatography (eluent: toluene/acetone 4:1).

R$_f$=0.64 (CH$_2$Cl$_2$/CH$_3$OH 10:1)

Yield: 369 mg (88.4%)

Example 30

9-(2-Azido-5-phenyl-3-pentyl)-2-(2-n-propoxy-phenyl)-purin-6-one

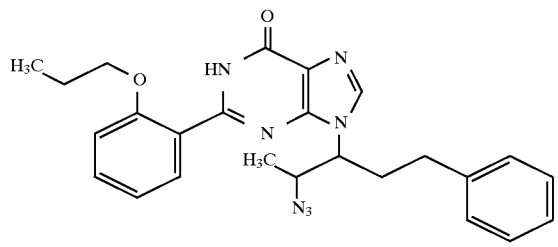

The title compound is prepared analogously to the instructions of Example 29, starting from 9-(2-methanesulphonyloxy-5-phenyl-3-pentyl)-2-(2-n-propoxyphenyl)-purin-6-one (Example 23).

R$_f$=0.54 (CH$_2$Cl$_2$/CH$_3$OH 10:1)

Yield: 87.4%

Example 31

9-(2-Azido-6-phenyl-3-hexyl)-2-(2-n-propoxyphenyl)-purin-6-one

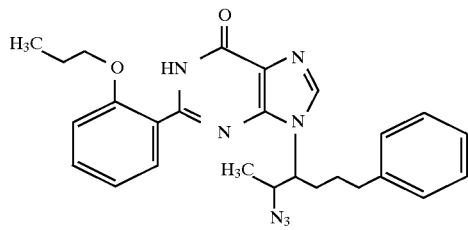

The title compound is prepared analogously to the instructions of Example 29, starting from 9-(2-methanesulphonyloxy-6-phenyl-3-hexyl)-2-(2-n-propoxyphenyl)-purin-6-one (Example 24).

R$_f$=0.55 (CH$_2$Cl$_2$/CH$_3$OH 10:1)

Yield: 74.9%

Example 32

9-(2-Azido-7-phenyl-3-heptyl)-2-(2-n-propoxyphenyl)-purin-6-one

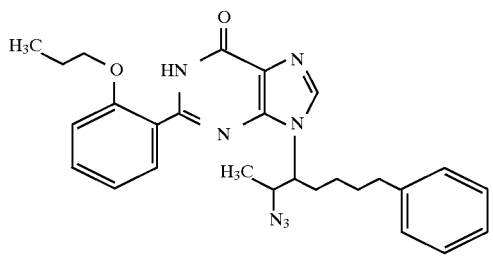

The title compound is prepared analogously to the instructions of Example 29, starting from 9-(2-methanesulphonyloxy-7-phenyl-3-heptyl)-2-(2-n-propoxyphenyl)-purin-6-one (Example 25).

R$_f$=0.6 (CH$_2$Cl$_2$/CH$_3$OH 10:1)

Yield: 67

Example 33

9-(2-Azido-8-phenyl-3-octyl)-2-(2-n-propoxyphenyl)-purin-6-one

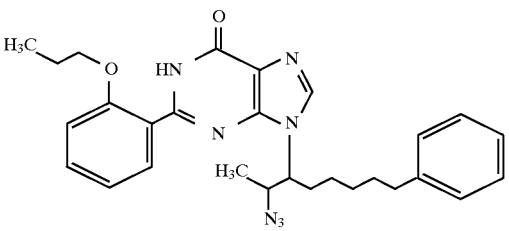

The title compound is prepared analogously to the instructions of Example 29, starting from 9-(2-methanesulphonyloxy-8-phenyl-3-octyl)-2-(2-n-propoxyphenyl)-purin-6-one (Example 26).

R$_f$=0.61 (CH$_2$Cl$_2$/CH$_3$OH 10:1)

Yield: 88%

Example 34

9-(1-Azido-5-phenyl-2-pentyl)-2-(2-n-propoxyphenyl)-purin-6-one

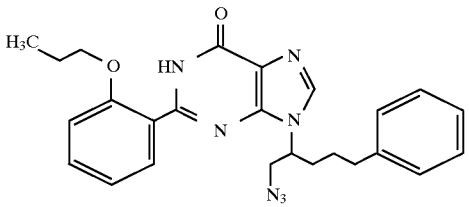

The title compound is prepared analogously to the instructions of Example 29, starting from 9-(1-methanesulphonyloxy-5-phenyl-2-pentyl)-2-(2-n-propoxyphenyl)-purin-6-one (Example 27).

R$_f$=0.56 (CH$_2$Cl$_2$/MeOH 10:1)

Yield: 98

Example 35

9-(2-Azido-3-nonyl)-2-(2-n-propoxy-5-morpholinesulphonyl-phenyl)-purin-6-one

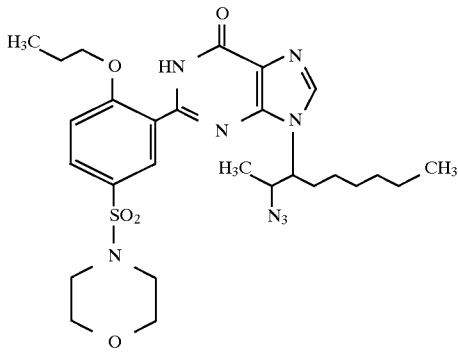

The title compound is prepared analogously to the instructions of Example 29, starting from 9-(2-methanesulphonyloxy-3-nonyl)-2-(2-n-propoxy-5-morpholinesulphonyl-phenyl)-purin-6-one (Example 28).

$R_f$=0.55 ($CH_2Cl_2/CH_3OH$ 10:1)

Yield: 38%

Example 36

9-(2-Amino-3-nonyl)-2-(2-n-propoxyphenyl)-purin-6-one

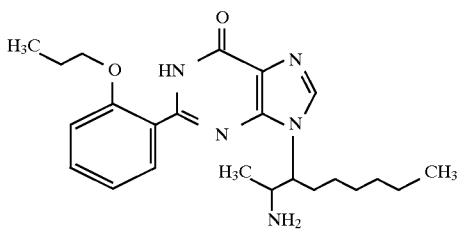

5.3 g (12.13 mmol) of 9-(2-azido-3-nonyl)-2-(2-n-propoxyphenyl)-purin-6-one (Example 29) are hydrogenated in 70 ml of absolute methanol in the presence of 0.1 g of Pd/C (10%) with hydrogen under normal pressure at room temperature. After 4 hours, the catalyst is filtered off, the solvent is distilled off in vacuo and the residue is purified by flash chromatography over silica gel (eluent: $CH_2Cl_2$/$CH_3OH$ 20:1).

$R_f$=0.28 ($CH_2Cl_2/CH_3OH$ 10:1)

Yield: 4.1 g (82.3%)

Example 37

9-(2-Acetamido-3-nonyl)-2-(2-n-propoxyphenyl)-purin-6-one

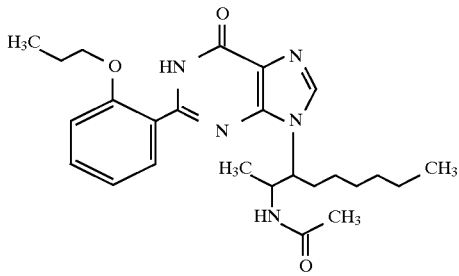

210 mg (0.5 mmol) of 9-(2-amino-3-nonyl)-2-(2-n-propoxyphenyl)-purin-6-one (Example 36) are dissolved in 20 ml of absolute $CH_2Cl_2$. 101 mg (1 mmol) of triethylamine are added at room temperature, and 78 mg (1 mmol) of acetyl chloride in 2 ml of absolute $CH_2Cl_2$ are then added dropwise. After 1 hour at room temperature, the organic phase is extracted by shaking with 10 ml of 2N HCl and with 10 ml of saturated $NaHCO_3$ solution. After the organic phase has been dried over $Na_2SO_4$, the solvent is evaporated in vacuo and the residue is purified by flash chromatography (eluent: $CH_2Cl_2/CH_3OH$ 40:1).

$R_f$=0.37 ($CH_2Cl_2/CH_3OH$ 10:1)

Yield: 174 mg (77%)

Example 38

9-(2-Benzoylamino-3-nonyl)-2-(2-n-propoxyphenyl)-purin-6-one

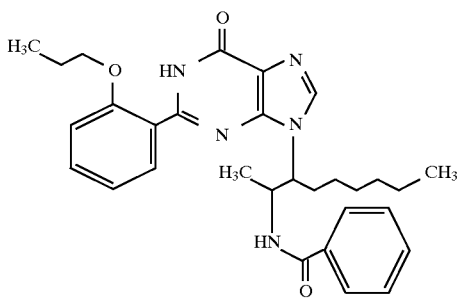

The title compound is prepared analogously to the instructions of Example 37 starting from 9-(2-amino-3-nonyl)-2-(2-n-propoxyphenyl)-purin-6-one (Example 36) and benzoyl chloride.

Melting point: 184° C. (toluene)

Yield: 59%

Example 39

9-(2-Methylsulphonylamino-3-nonyl)-2-(2-n-propoxyphenyl)-purin-6-one

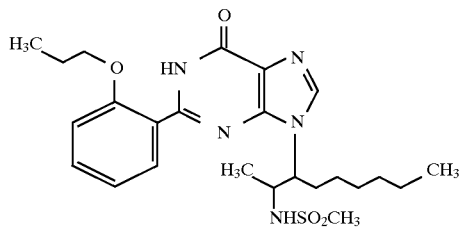

The title compound is prepared analogously to the instructions of Example 37, starting from 9-(2-amino-3-nonyl)-2-(2-n-propoxyphenyl)-purin-6-one (Example 36) and methylsulphonyl chloride.
$R_f$=0.46 (CH$_2$Cl$_2$/CH$_3$OH 10:1)
Yield: 78.2

Example 40

9-(2-Phenylsulphonylamino-3-nonyl)-2-(2-n-propoxyphenyl)-purin-6-one

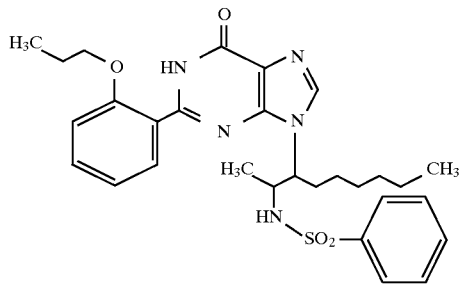

The title compound is prepared analogously to the instructions of Example 37, starting from 9-(2-amino-3-nonyl)-2-(2-n-propoxyphenyl)-purin-6-one (Example 36) and phenylsulphonyl chloride.
Melting point: 112° C. (toluene/ether)
Yield: 62.9%

Example 41

9-(2-Acetoxy-3-nonyl)-2-(2-n-propoxyphenyl)-purin-6-one

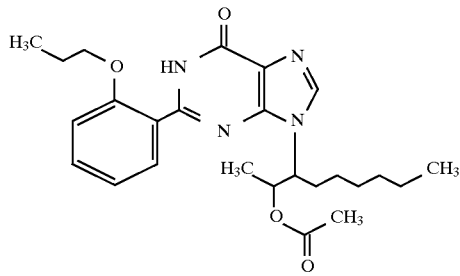

206 mg (0.5 mmol) of 9-(2-hydroxy-3-nonyl)-2-(2-n-propoxyphenyl)-purin-6-one (Example 3), 47 mg (0.6 mmol) of acetyl chloride, 47 mg (0.6 mmol) of pyridine and 5 mg of DMAP are stirred in 10 ml of absolute CH$_2$Cl$_2$ at 25° C. for 1 hour and then at 40° C. for 1 hour. The mixture is extracted by shaking twice with 10 ml of 2N HCl solution each time and twice with 10 ml of saturated NaHCO$_3$ solution each time and washed once with saturated NaCl solution. After the organic phase has been dried over Na$_2$SO$_4$, the solvent is evaporated in vacuo and the residue is dried under a high vacuum.

$R_f$=0.53 (CH$_2$Cl$_2$/CH$_3$OH 100:1)

Yield: 90.5%

Example 42

9-(1-Acetoxy-2-octyl)-2-(2-n-propoxyphenyl)-purin-6-one

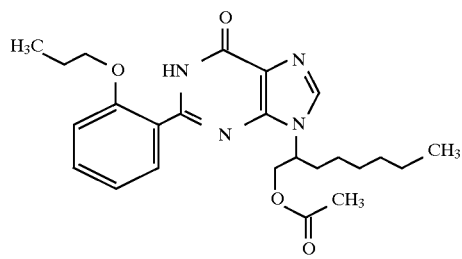

The title compound is prepared analogously to the instructions of Example 41, starting from 9-(1-hydroxy-2-octyl)-2-(2-n-propoxyphenyl)-purin-6-one (Example 2).

$R_f$=0.52 (CH$_2$Cl$_2$/CH$_3$OH 100:1)

Yield: 88.5

Example 43

9-(2-Benzoyloxy-3-nonyl)-2-(2-n-propoxyphenyl)-purin-6-one

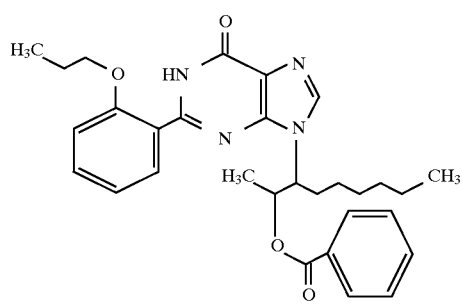

The title compound is prepared analogously to the instructions of Example 41, starting from 9-(2-hydroxy-3-nonyl)-2-(2-n-propoxyphenyl)-purin-6-one (Example 3) and benzoyl chloride.

$R_f$=0.57 (CH$_2$Cl$_2$/CH$_3$OH 100:1)

Yield: 89%

Example 44

9-(2-Methoxy-3-nonyl)-2-(2-n-propoxyphenyl)-purin-6-one

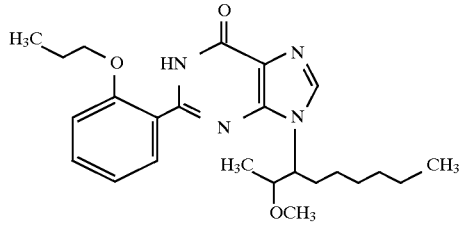

48 mg of 60% strength NaH (1.2 mmol) are suspended in 2 ml of absolute tetrahydrofuran at 20° C. 206 mg (0.5 mmol) of 9-(2-hydroxy-3-nonyl)-2-(2-n-propoxyphenyl)-purin-6-one (Example 3) in 3 ml of absolute tetrahydrofuran are added dropwise. After 15 minutes at 20° C.0, 85 mg (0.6 mmol) of methyl iodide in 3 ml of absolute tetrahydrofuran are added dropwise and the mixture is stirred overnight at 20° C. The solvent is removed on a rotary evaporator in vacuo, the residue is taken up in 10 ml of ethyl acetate and the mixture is washed with 20 ml of water. After the organic phase has been dried with $Na_2SO_4$, it is evaporated on a rotary evaporator and the product is purified by column chromatography (eluent: toluene/acetone 5:1).

$R_f$=0.58 ($CH_2Cl_2/CH_3OH$ 100:1)

Yield: 74.2%

Example 45

9-(2-Ethoxycarbonylmethyleneoxy-3-nonyl)-2-(2-n-propoxyphenyl)-purin-6-one

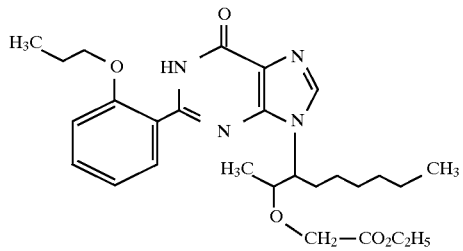

The title compound is prepared analogously to the instructions of Example 44 starting from 9-(2-hydroxy-3-nonyl)-2-(2-n-propoxyphenyl)-purin-6-one (Example 3) and ethyl bromoacetate.

$R_f$=0.55 ($CH_2Cl_2/CH_3OH$ 100:1)

Yield: 85.8

Example 46

9-(2-Carboxymethyleneoxy-3-nonyl)-2-(2-n-propoxyphenyl)-purin-6-one

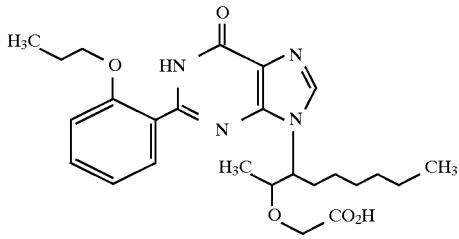

498 mg (1 mmol) of the ester from Example 45 are stirred in 4 ml of 1N NaOH and 5 ml of MeOH at 20° C. for 1 hour. The methanol is distilled off in vacuo. After addition of 5 ml of $H_2O$, the mixture is extracted by shaking with ethyl acetate. The aqueous phase is acidified with 4 ml of 2N HCl and extracted by shaking twice with 10 ml of ethyl acetate each time. The combined ethyl acetate phases are dried over $Na_2SO_4$ and evaporated.

$R_f$=0.27 ($CH_2Cl_2/CH_3OH$ 10:1)

Yield: 88.5%

Example 47

9-(2-Amidocarbonylmethyleneoxy-3-nonyl)-2-(2-n-propoxyphenyl)-purin-6-one

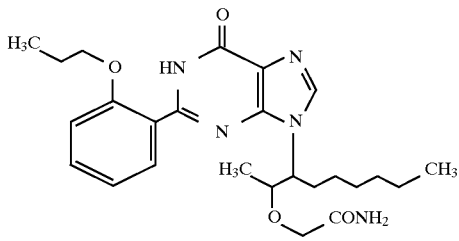

The title compound is prepared analogously to the instructions of Example 45, starting from 9-(2-hydroxy-3-nonyl)-2-(2-n-propoxyphenyl)-purin-6-one (Example 3) and bromoacetamide.

$R_f$=0.26 ($CH_2Cl_2/CH_3OH$ 10:1)

Yield: 31.6%

Example 48

9-(2-Oxo-3-nonyl)-2-(2-n-propoxyphenyl)-purin-6-one

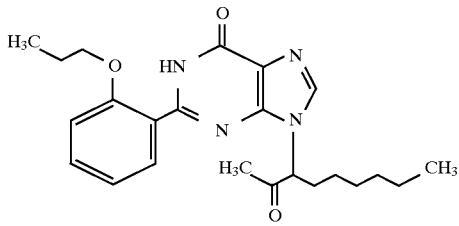

0.31 ml of absolute dimethyl sulphoxide (4.4 mmol) in 3 ml of absolute $CH_2Cl_2$ is added dropwise to 0.19 ml (2.2 mmol) of oxalyl chloride in 5 ml of $CH_2Cl_2$ at −60° C. in the course of 10 minutes and the mixture is subsequently stirred for 20 minutes. 824 mg (2 mmol) of 9-(2-hydroxy-3-methyl)-2-(2-n-propoxyphenyl)-purin-6-one (Example 3) in 5 ml of absolute $CH_2Cl_2$ are then added dropwise in the course of 45 minutes and the mixture is subsequently stirred at $-60°$ C. for 1 hour. 1.39 ml (10 mmol) of triethylamine in 5 ml of absolute $CH_2Cl_2$ are added dropwise to this solution in the course of 30 minutes and the mixture is subsequently stirred at $-60°$ C. for 15 minutes. It is allowed to come to $20°$ C., 10 ml of $H_2O$ are added, the phases are separated and the organic phase is washed with 20 ml of saturated NaCl solution. After the mixture has been dried over $Na_2SO_4$, it is evaporated and the residue is purified by flash chromatography (eluent: $CH_2Cl_2/CH_3OH$ 40:1).
Melting point: $83°$ C. (ether/cyclohexane)
Yield: 535 mg (65.2%)

Example 49

9-(2-Ethyloximino-3-nonyl)-2-(2-n-propoxyphenyl)-purin-6-one

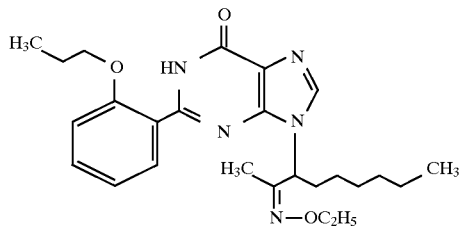

412 mg (1 mmol) of 9-(2-oxo-3-nonyl)-2-(2-n-propoxyphenyl)-purin-6-one (Example 48) are dissolved in 10 ml of methanol, and 117 mg (1.2 mmol) of ethylhydroxylamine hydrochloride, dissolved in 1.5 ml of water, are added. The mixture is boiled under reflux for 2 hours, cooled and evaporated in vacuo. The residue is taken up in 10 ml of ethyl acetate and washed with 10 ml of saturated $NaHCO_3$ solution. After the organic phase has been dried with $Na_2SO_4$, the solvent is distilled off in vacuo and the residue is purified by flash chromatography (eluent: toluenelacetone 4:1).
$R_f$=0.53 (toluene/acetone 1:1)
Yield: 366 mg (80.8%)

The oximes listed in Table III are prepared in accordance with these instructions using the corresponding hydroxylamine hydrochlorides (all the oximes are in the form of cis/trans mixtures).

TABLE III

| Example No. | $R^{20}$ | Yield (% of theory) | Melting point (°C)/$R_f$ |
|---|---|---|---|
| 50 | H | 69.4 | 111 |
| 51 | $C(CH_3)_3$ | 79.4 | 0.56[a] |

TABLE III-continued

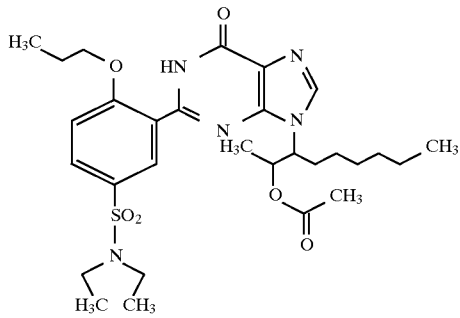

| Example No. | $R^{20}$ | Yield (% of theory) | Melting point (°C)/$R_f$ |
|---|---|---|---|
| 52 | $-CH_2-C_6H_5$ | 98.4 | 0.55[a] |
| 53 | $-CH_2CH_2-N(C_2H_5)_2$ | 70.2 | 0.29[b] |

[a] Mobile phase: toluene/acetone 1:1
[b] Mobile phase: $CH_2Cl_2$/MeOH 10:1

Example 54

9-(2-Acetoxy-3-nonyl)-2-(2-n-propoxy-5-diethylaminosulphonyl-phenyl)-purin-6-one 1.28 g (2.82 mmol) of 9-(2-acetoxy-3-nonyl)-2-(2-n-propoxyphenyl)-purin-6-one (Example 41) are added in portions to 4 ml of chlorosulphonic acid at $0°$ C. and the mixture is stirred overnight at $20°$ C. The batch is added dropwise to 30 ml of ice-water and the aqueous phase is extracted twice with 20 ml of ethyl acetate each time. The combined organic phases are dried over $Na_2SO_4$ and the solvent is distilled off in vacuo.
Yield: 0.9 g (57.8%)
$R_f$=0.52 ($CH_2Cl_2/CH_3OH$ 10:1)

The residue is taken up in 30 ml of absolute ethanol without further purification, 5.1 ml of diethylamine are added and the mixture is stirred at $25°$ C. for 6 hours (monitoring by thin-layer chromatography). The ethanol is distilled off in vacuo, the residue is taken up in 50 ml of ethyl acetate and the mixture is washed twice with 50 ml of $H_2O$ each time. After drying over $Na_2SO_4$, the organic phase is evaporated in vacuo and the residue is purified by flash chromatography (eluent: toluene/acetone 3:1).
$R_f$=0.52 ($CH_2Cl_2/CH_3OH$ 10:1)
Yield: 549 mg (57.2%)

The compounds listed in Table IV are prepared analogously to the instructions of Example 54 from the corresponding purinone and the corresponding amine:

TABLE IV

| Example No. | X | A | Yield (% of theory) | Melting point (°C.)/$R_f$ |
|---|---|---|---|---|
| 55 | —N(morpholine) | H₃C—CH(CH₃)—CH(OCO—CH₃)—(CH₂)₄—CH₃ | 37.4 | 0.53[a] |
| 56 | —N(C₂H₅)₂ | H₃C—CH₂—CH(—)—(CH₂)₄—CH₃ with CH₃ branch | 72.3 | 0.58[a] |
| 57 | —N(morpholine) | H₃C—CH(CH₃)—(CH₂)₄—CH₃ | 80.9 | 0.51[a] |
| 58 | —N(piperazine-N-CH₂CH₂OH) | H₃C—CH(CH₃)—(CH₂)₄—CH₃ | 78.4 | 0.39[a] |
| 59 | —N(morpholine) | H₃C—CH(CH₃)—(CH₂)₄—CH₃ | 35.9 | 0.3[b] |
| 60 | —N(morpholine) | H₃C—CH(CH(CH₃)₂)—(CH₂)₄—CH₃ | 58 | 0.52[a] |
| 61 | —N(morpholine) | H₃C—CH(CH₃)—CH₂—CH₂—C₆H₄—SO₃—N(morpholine) | 41 | 0.27[b] |
| 62 | —N(morpholine) | H₃C—CH(CH₃)—CH₂—CH₂—CH₂—C₆H₄—SO₃—N(morpholine) | 26.5 | 0.33[b] |
| 63 | —N(morpholine) | H₃C—CH(CH₃)—CH(CH₃)—(CH₂)₄—C₆H₄—SO₃—N(morpholine) | 76.3 | 0.35[b] |
| 64 | —N(morpholine) | H₃C—CH(OCO—CH₃)—CH(CH₃)—(CH₂)₄—C₆H₄—SO₃—N(morpholine) | 37 | 0.39[b] |

TABLE IV-continued a) Mobile phase: CH$_2$Cl$_2$/CH$_3$OH 10:1
b) Mobile phase: toluene/acetone 1:1

Example 65

9-(2-Hydroxy-3-nonyl)-2-(2-n-propoxy-5-diethylaminosulphonyl-phenyl)-purin-6-one 140 mg(0.24 mmol)of 5-(2-acetoxy-3-nonyl)-2-(2-n-propoxy-5-diethylarninosulphonyl-phenyl)-purin-6-one (Example 54) are dissolved in 5 ml of methanol. After addition of 0.5 ml of aqueous 1N NaOH solution, the mixture is stirred at 25° C. for 2 hours. 0.25 ml of aqueous 2N HCl solution is added, the methanol is distilled off in vacuo and 10 ml of ethyl acetate and 10 ml of water are added. The organic phase is separated off, dried over Na$_2$SO$_4$ and evaporated. The residue is purified by flash chromatography (eluent: CH$_2$Cl$_2$/CH$_3$OH 40:1).

R$_f$=0.47 (CH$_2$Cl$_2$/CH$_3$OH 10:1)
Yield: 112 mg (85%)

Example 66

9-(2-Hydroxy-3-nonyl)-2-(2-n-propoxy-5-morpholinosulphonylphenyl)-purin-6-one

The title compound is prepared analogously to the instructions of Example 65, starting from-(2-acetoxy-3-nonyl)-2-(2-n-propoxy-5-morpholinosulphonyl-phenyl)-purin-6-one (Example 55).
R$_f$=0.45 (CH$_2$Cl$_2$/CH$_3$OH 10:1)
Yield: 80.6%

Example 67

9-(2-Hydroxy-8-(4-morpholinosulphonyl-phenyl)-3-octyl)-2-(2-n-propoxy-5-morpholinosulphonyl-phenyl)-purin-6-one

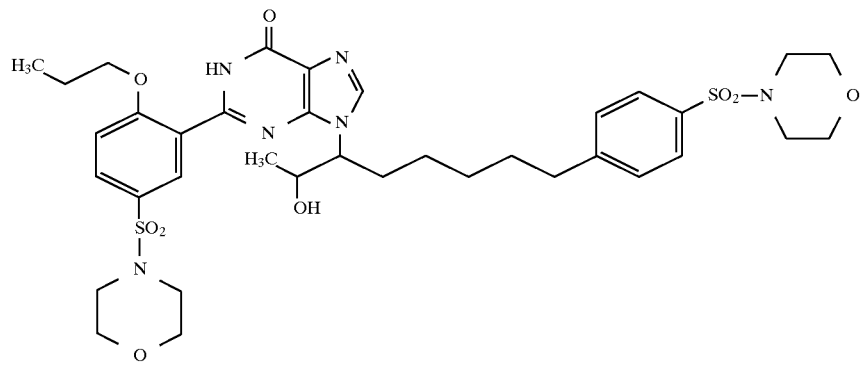

The title compound is prepared analogously to the instructions of Example 65, starting from 9-(2-acetoxy-8-(4-morpholinosulphonyl-phenyl)-3-octyl)-2-(2-n-propoxy-5-morpholinosulphonyl-phenyl)-purin-6-one (Example 64).
$R_f$=0.35 (toluene/acetone 1:1)
Yield: 79.6%

Example 68

9-(2-Oxo-3-nonyl)-2-(2-n-propoxy-5-morpholinosulphonyl-phenyl)-purin-6-one

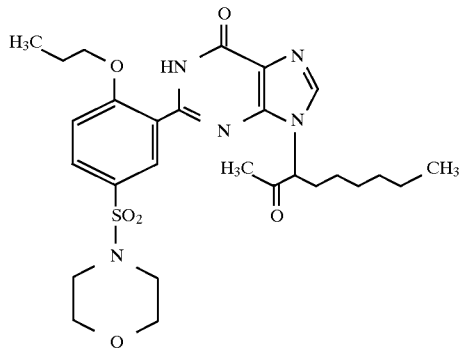

The title compound is prepared analogously to the instructions of Example 48 starting from 9-(2-hydroxy-3-nonyl)-2-(2-n-propoxy-5-morpholinosulphonyl-phenyl)-purin-6-one (Example 66).
$R_f$=0.52 (CH$_2$Cl$_2$/CH$_3$OH 10:19)
Yield: 63.2%

Example 69

9-(2-Oxo-8-(4-morpholinosulphonyl-phenyl)-3-octyl)-2-(2-n-propoxy-5-morpholinosulphonyl-phenyl)-purin-6-one

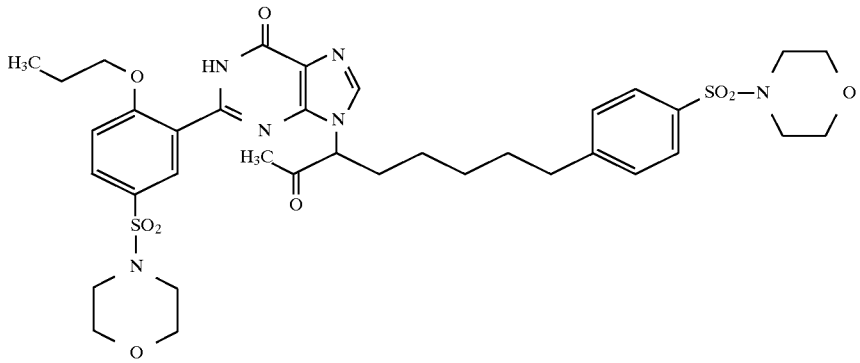

The title compound is prepared analogously to the instructions of Example 48, starting from 9-(2-hydroxy-8-(4-morpholinosulphonyl-phenyl)-3-octyl)-2-(2-n-propoxy-5-morpholinosulphonyl-phenyl)-purin-6-one (Example 67).

$R_f$=0.41 (toluene/acetone 1:1)

Yield: 51.1

Example 70

9-(2-Oxo-6-phenyl-3-hexyl)-2-(2-n-propoxy-5-morpholinosulphonyl-phenyl)-purin-6-one

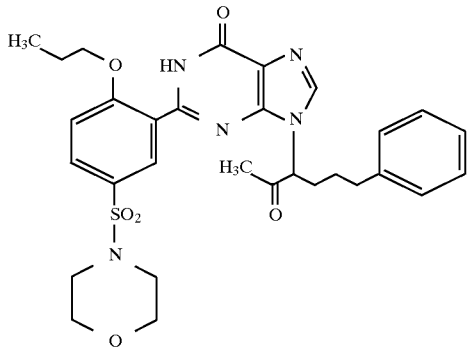

The title compound is prepared analogously to the instructions of Example 48, starting from 9-(2-hydroxy-6-phenyl-3-hexyl)-2-(2-n-propoxy-5-morpholinosulphonyl-phenyl)-purin-6-one (Example 20).

$R_f$=0.6 (CH$_2$Cl$_2$/CH$_3$OH 10: 1)

Yield: 51%.

We claim:

1. 9-Substituted 2-(2-n-alkoxyphenyl)purin-6-ones of the formula (I)

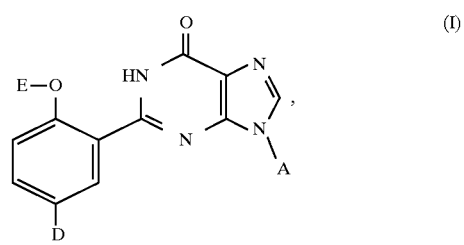

in which

A represents a radical of the formula

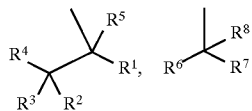

wherein,
a denotes a number 9, 10, 11, 12, 13, 14 or 15, $R^1$ denotes straight-chain or branched alkyl having 2 to 10 carbon atoms, which is optionally substituted by phenyl, which in turn can be substituted by halogen, nitro, cyano, by straight-chain or branched alkyl having up to 6 carbon atoms or by a group of the formula $-SO_2-NR^9R^{10}$, wherein
$R^9$ and $R^{10}$ are identical or different and denote hydrogen, phenyl or straight-chain or branched alkyl having up to 6 carbon atoms, which is optionally substituted by hydroxyl, or together with the nitrogen atom form a 5- to 6-membered, saturated heterocyclic radical which has up to 2 further heteroatoms from the series consisting of S, N and/or O and is optionally substituted, including via a free N function, by straight-chain or branched alkyl having up to 6 carbon atoms, which in turn can be substituted by hydroxyl, or is alkyl optionally substituted by a group of the formula $-NR^{11}R^{12}$,
wherein
$R^{11}$ and $R^{12}$ have the abovementioned meaning of $R^9$ and $R^{10}$ and are identical to or different from these, $R^2$ denotes hydrogen, azido, straight-chain or branched alkyl having up to 6 carbon atoms or a group of the formula $-OR^{13}$, $O-SO_2R^{14}$ or $-NR^{15}R^{16}$, wherein
$R^{13}$ is hydrogen, a hydroxyl-protecting group, straight-chain or branched alkanoyl having up to 6 carbon atoms, benzoyl or straight-chain or branched alkyl having up to 6 carbon atoms, which is optionally substituted by carboxyl or straight-chain or branched alkoxy carbonyl having up to 6 carbon atoms or by a group of the formula $-CO-NR^{17}R^{18}$,
wherein
$R^{17}$ and $R^{18}$ are identical or different and denote hydrogen or straight-chain or branched alkyl having up to 4 carbon atoms, $R^{14}$ denotes straight-chain or branched alkyl having up to 4 carbon atoms or phenyl, $R^{15}$ and $R^{16}$ are identical or different and denote hydrogen, an amino-protecting group, straight-chain or branched alkyl or alkanoyl having in each case up to 6 carbon atoms, formyl, benzoyl or a group of the formula $-SO_2R^{19}$,
wherein
$R^{19}$ has the abovementioned meaning of $R^{14}$ and is identical to or different from this, $R^3$ denotes hydrogen, or
$R^2$ and $R^3$ together form a radical of the formula =O or $=N-OR^{20}$,
wherein
$R^{20}$ denotes hydrogen or straight-chain or branched alkyl having up to 6 carbon atoms, which is optionally substituted by phenyl or by a group of the formula $-NR^{21}R^{22}$, wherein $R^{21}$ and $R^{22}$ are identical or different and denote hydrogen, phenyl or straight-chain or branched alkyl having up to 6 carbon atoms, $R^4$ denotes hydrogen or straight-chain or branched alkyl having up to 4 carbon atoms, $R^5$ and $R^8$ are identical or different and denote hydrogen or straight-chain or branched alkyl having up to 3 carbon atoms, $R^6$ denotes hydrogen or straight-chain or branched alkyl having up to 5 carbon atoms, which is optionally substituted by hydroxyl, $R^7$ denotes straight-chain or branched alkyl having 2 to 8 carbon atoms, which is substituted by a group of the formula $-NR^{23}R^{24}$, wherein
$R^{23}$ and $R^{24}$ are identical or different and denote hydrogen or straight-chain or branched alkyl having up to 5 carbon atoms, which is optionally substituted by hydroxyl, or is substituted by phenyl, which in turn is substituted by the group of the formula $-SO_2-NR^{25}R^{26}$,
wherein
$R^{25}$ and $R^{26}$ have the abovementioned meaning of $R^9$ and $R^{10}$, D represents hydrogen or represents a group of the formula $-SO_2-NR^{27}R^{28}$, wherein
$R^{27}$ and $R^{28}$ are identical or different and have the abovementioned meaning of $R^9$ and $R^{10}$ and are identical to or different from these, and E represents straight-chain or branched alkyl having up to 8 carbon atoms, and tautomers and salts thereof, with the proviso that if A=alkyl then the alkyl has at least 8 carbon atoms.

2. 9-Substituted 2-(2-n-alkoxyphenyl)purin-$^6$-ones of the formula (1) according to claim 1, in which A represents a radical of the formula

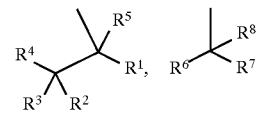

wherein,
a denotes a number 9, 10, 11, 12 or 13, $R^1$ denotes straight-chain or branched alkyl having 2 to 8 carbon atoms, which is optionally substituted by phenyl, which in turn can be substituted by fluorine, chlorine, bromine, nitro, cyano, by straight-chain or branched alkyl having up to 4 carbon atoms or by a group of the formula $-SO_2-NR^9R^{10}$, wherein
$R^9$ and $R^{10}$ are identical or different and denote hydrogen, phenyl or straight-chain or branched alkyl having up to 5 carbon atoms, which is optionally substituted by hydroxyl, or, together with the hydrogen atom, form a morpholinyl, pyrrolidinyl or piperidinyl ring or a piperazinyl ring, which is optionally substituted, including via a free NH function, by straight-chain or branched alkyl having up to 3 carbon atoms, which in turn can be substituted by hydroxyl, or is alkyl optionally substituted by a group of the formula $-NR^{11}R^{12}$,
wherein
$R^{11}$ and $R^{12}$ have the abovementioned meaning of $R^9$ and $R^{10}$ and are identical to or different from these, $R^2$ denotes hydrogen, azido, straight-chain or branched alkyl having up to 4 carbon atoms or a group of the formula —$OR^{13}$, —O—$SO_2$—$R^{14}$ or —$NR^{15}R^{16}$,
wherein
$R^{13}$ denotes hydrogen, benzyl, straight-chain or branched alkanoyl having up to 4 carbon atoms, benzoyl or straight-chain or branched alkyl having up to 4 carbon atoms, which is optionally substituted by carboxyl or straight-chain or branched alkoxy carbonyl having up to 4 carbon atoms or by a group of the formula —CO—$NR^{17}R^{18}$,
wherein
$R^{17}$ and $R^{18}$ are identical or different and denote hydrogen or straight-chain or branched alkyl having up to 3 carbon atoms,
$R^{14}$ denotes straight-chain or branched alkyl having up to 3 carbon atoms or phenyl,
$R^{15}$ and $R^{16}$ are identical or different and denote hydrogen, tert-butoxycarbonyl, benzyloxycarbonyl or straight-chain or branched alkyl or alkanovl having in each case up to 4 carbon atoms, formyl, benzoyl or a group of the formula —$SO_2R^{19}$,
wherein
$R^{19}$ has the abovementioned meaning of $R^{14}$ and is identical to or different from this,
$R^3$ denotes hydrogen, or
$R^2$ and $R^3$ together form a radical of the formula =O or =N—$OR^{20}$,
wherein
$R^{20}$ denotes hydrogen or straight-chain or branched alkyl having up to 4 carbon atoms, which is optionally substituted by phenyl or by a group of the formula —$NR^{21}R^{22}$,
wherein
$R^{21}$ and $R^{22}$ are identical or different and denote hydrogen, phenyl or straight-chain or branched alkyl having up to 4 carbon atoms,
$R^4$ denotes hydrogen or straight-chain or branched alkyl having up to 3 carbon atoms,
$R^5$ and $R^8$ are identical or different and denote hydrogen or methyl,
$R^6$ denotes hydrogen or straight-chain or branched alkyl having up to 3 carbon atoms, which is optionally substituted by hydroxyl,
$R^7$ denotes straight-chain or branched alkyl having 2 to 6 carbon atoms, which is substituted by a group of the formula —$NR^{23}R^{24}$,
wherein
$R^{23}$ and $R^{24}$ are identical or different and denote hydrogen or straight-chain or branched alkyl having up to 4 carbon atoms, which is optionally substituted by hydroxyl,
or is substituted by phenyl, which in turn is substituted by a group of the formula —$SO_2$—$NR^{25}R^{26}$,
wherein
$R^{25}$ and $R^{26}$ are identical or different and have the abovementioned meaning of $R^9$ and $R^{10}$,
D represents hydrogen, or represents a group of the formula —$SO_2$-$NR^{27}R^{28}$,
wherein
$R^{27}$ and $R^{28}$ are identical or different and have the abovementioned meaning of $R^9$ and $R^{10}$ and are identical to or different from these, and
E represents straight-chain or branched alkyl having up to 6 carbon atoms,
and tautomers and salts thereof,
with the proviso that if A=alkyl, then the alkyl has at least 8 carbon atoms.

3. 9-Substituted 2-(2-n-alkoxyphenyl)purin-6-ones of the formula according to claim 1,
wherein
A represents a radical of the formula

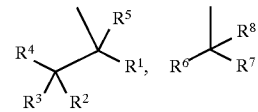

wherein,
a denotes a number 9, 10, 11 or 12,
$R^1$ denotes straight-chain or branched alkyl having 2 to 7 carbon atoms, which is optionally substituted by phenyl, which in turn can be substituted by fluorine, chlorine, bromine, nitro, cyano, by straight-chain or branched alkyl having up to 3 carbon atoms or by a group of the formula —$SO_2$—$NR^9R^{10}$,
wherein
$R^9$ and $R^{10}$ are identical or different and denote hydrogen, phenyl or straight-chain or branched alkyl having up to 4 carbon atoms, which is optionally substituted by hydroxyl, or, together with the nitrogen atom, form a morpholinyl, pyrrolidinyl or piperidinyl ring or a piperazinyl ring, which is optionally substituted, including via free NH function, by straight-chain or branched alkyl having up to 3 carbon atoms, which in turn can be substituted by hydroxyl, or
is alkyl optionally substituted by a group of the formula —$NR^{11}R^{12}$,
wherein
$R^{11}$ and $R^{12}$ have the abovementioned meaning of $R^9$ and $R^{10}$ and are identical to or different from these,
$R^2$ denotes hydrogen, azido, straight-chain or branched alkyl having up to 3 carbon atoms or a group of the formula —$OR^{13}$, —$OSO_2R^{14}$ or —$NR^{15}R^{16}$,
wherein
$R^{13}$ denotes hydrogen, straight-chain or branched alkanoyl having up to 3 carbon atoms, benzoyl or straight-chain or branched alkyl having up to 3 carbon atoms, which is optionally substituted by carboxyl or straight-chain or branched alkoxycarbonyl having up to 3 carbon atoms or by a group of the formula —CO—$NR^{17}R^{18}$,
wherein
$R^{17}$ and $R^{18}$ are identical or different and denote hydrogen, methyl or ethyl,
$R^{14}$ denotes straight-chain or branched alkyl having up to 3 carbon atoms or phenyl,
$R^{15}$ and $R^{16}$ are identical or different and denote hydrogen tert-butoxycarbonyl, straight-chain or branched alkyl or alkanoyl having in each case up to 3 carbon atoms, formyl, benzoyl or a group of the formula —$SO_2R^{19}$,
wherein
$R^{19}$ has the abovementioned meaning of $R^{14}$ and is identical to or different from this,
$R^3$ denotes hydrogen, or
$R^2$ and $R^3$ together form a radical of the formula =O or =N—$OR^{20}$,
wherein
$R^{20}$ denotes hydrogen or straight-chain or branched alkyl having up to 4 carbon atoms, which is optionally substituted by phenyl or by a group of the formula —$NR^{21}R^{22}$,
wherein $R^{21}$ and $R^{22}$ are identical or different and denote hydrogen, phenyl or straight-chain or branched alkyl having up to 3 carbon atoms, $R^4$ denotes hydrogen or straight-chain or branched alkyl having up to 3 carbon atoms, $R^5$ and $R^8$ are identical or different and denote hydrogen or methyl, $R^6$ denotes hydrogen or straight-chain or branched alkyl having up to 3 carbon atoms, which is optionally substituted by hydroxyl, $R^7$ denotes straight-chain or branched alkyl having 2 to 6 carbon atoms, which is substituted by a group of the formula —$NR^{23}R^{24}$, wherein $R^{23}$ and $R^{24}$ are identical or different and denote hydrogen or straight-chain or branched alkyl having up to 3 carbon atoms, which is optionally substituted by hydroxyl, or is substituted by phenyl, which in turn is substituted by the group of the formula —$SO_2$—$R^{25}R^{26}$, wherein $R^{25}$ and $R^{26}$ have the abovementioned meaning of $R^9$ and $R^{10}$, D represents hydrogen, or represents a group of the formula —$SO_2$—$NR^{27}R^{28}$, wherein $R^{27}$ and $R^{28}$ are identical or different and have the abovementioned meaning of $R^9$ and $R^{10}$ and are identical to or different from these, and E represents straight-chain or branched alkyl having up to 5 carbon atoms, and tautomers and salts thereof, with the proviso that if A=alkyl then the alkyl has at least 8 carbon atoms.

4. 9-substituted 2-(2-n-alkoxyphenyl)purin-6-ones according to claim 1 wherein such compound is 9-(2-Azido-3-nonyl)-2-(2-n-propoxyphenyl)-purin-6-one of the formula

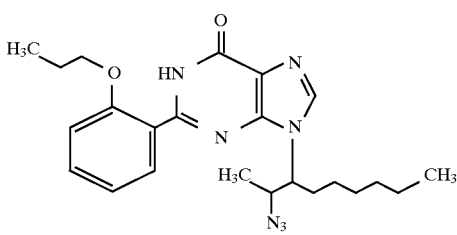

and salts thereof.

5. 9-substituted 2-(2-n-alkoxyphenyl)purin-6-ones according to claim 1 wherein such compound is 9-(2-Azido-6-phenyl-3-hexyl)-2-(2-n-propoxyphenyl)-purin-6-one of the formula

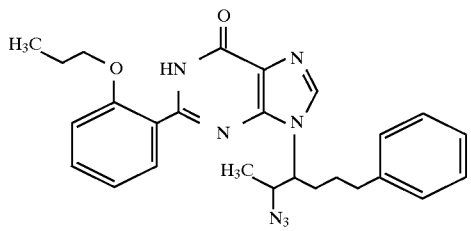

and tautomers and salts thereof.

6. 9-substituted 2-(2-n-alkoxyphenyl)purin-6-ones according to claim 1 wherein such compound is 9-(2-Benzoylamino-3-nonyl)-2-(2-n-propoxyphenyl)-purin-6-one of the formula

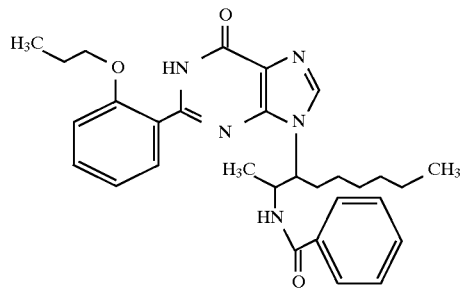

and tautomers and salts thereof.

7. 9-substituted 2-(2-n-alkoxyphenyl)purin-6-ones according to claim 1 wherein such compound is 9-(2-octyl)-2-(2-n-propoxy-5-morpholinosulfonylphenyl)-purin-6-one of the formula

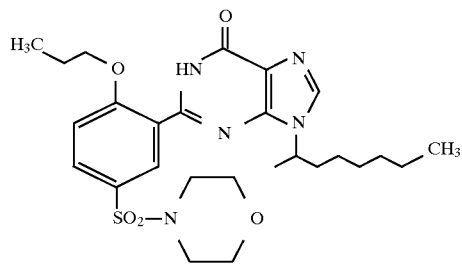

and tautomers and salts thereof.

8. 9-substituted 2-(2-n-alkoxyphenyl)purin-6-ones according to claim 1 wherein such compound is 9-(2-hydroxy-3-nonyl)-2-(2-n-propoxyphenyl)-purin-6-one of the formula

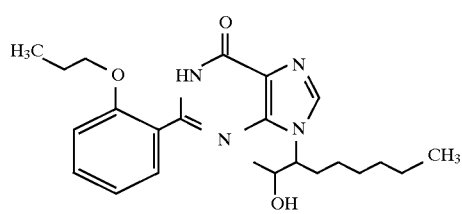

and tautomers and salts thereof.

9. 9-substituted 2-(2-n-alkoxyphenyl)purin-6-ones according to claim 1 wherein such compound is 9-(2-hydroxy-6-phenyl-3-hexyl)-2-(2-n-propoxyphenyl)-purin-6-one of the formula

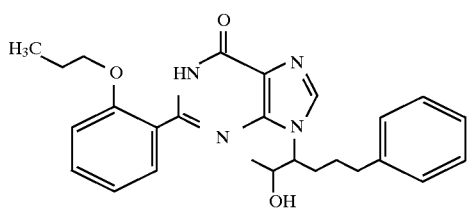

and tautomers and salts thereof.

10. 9-substituted 2-(2-n-alkoxyphenyl)purin-6-ones according to claim 1 wherein such compound is 9-(5-phenyl-2-pentyl)-2-(2-n-propoxyphenyl)-purin-6-one of the formula

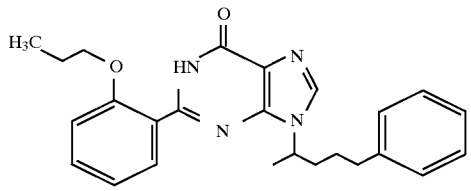

and tautomers and salts thereof.

11. 9-substituted 2-(2-n-alkoxyphenyl)purin-6-ones according to claim 1 wherein such compound is 9-(2-methyl-6-phenyl-3-hexyl)-2-(2-n-propoxyphenyl)-purin-6-one of the formula

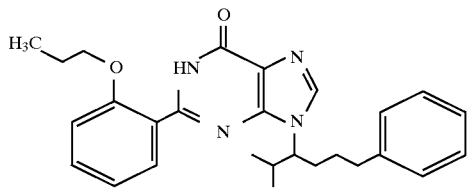

and tautomers and salts thereof.

12. 9-substituted 2-(2-n-alkoxyphenyl)purin-6-ones according to claim 1 wherein such compound is 9-(5-phenyl)-2-pentyl-2-(2-n-propoxy-5-morpholinosulfonylphenyl)-purin-6-one of the formula

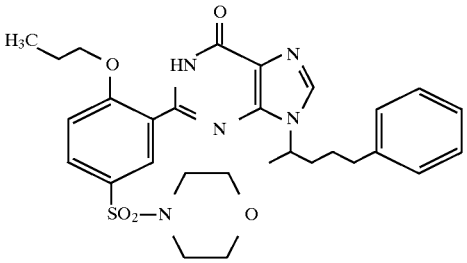

and tautomers and salts thereof.

13. The method of treating impotence in a patient in need thereof which comprises administering to such patient an amount effective therefor of the compound or a tautomer or salt thereof according to claim 1.

14. A pharmaceutical composition comprising the compound or a tautomer or salt thereof according to claim 1 and a pharmaceutically acceptable extender.

15. The method of treating prostate hypertrophy which comprises administering to a patient in need thereof an amount effective therefor of the compound or a tautomer or salt thereof according to claim 1.

16. The method of treating incontinence which comprises administering to a patient in need thereof an amount effective therefor of the compound or a tautomer or salt thereof according to claim 1.

* * * * *

UNITED STATES PATENT AND TRADEMARK OFFICE
CERTIFICATE OF CORRECTION

PATENT NO. : 5,866,571
DATED : February 2, 1999
INVENTOR(S) : Ulrich Niewohner, et. al.

It is certified that error appears in the above-identified patent and that said Letters Patent is hereby corrected as shown below:

Title Page            [30] Foreign Application Priority Data:
Delete "April" and substitute --January--

Col. 43, Line 3          Insert --or-$(CH_2)_q$-$CH_3$--

Col. 44, Line 40         Insert --or -$(CH_2)_q$-$CH_3$--

Signed and Sealed this

Fifth Day of December, 2000

Attest:

Q. TODD DICKINSON

*Attesting Officer*        *Director of Patents and Trademarks*